US008815889B2

(12) United States Patent
Cowley et al.

(10) Patent No.: US 8,815,889 B2

(45) **Date of Patent: *Aug. 26, 2014**

(54) COMPOSITIONS AND METHODS FOR INCREASING INSULIN SENSITIVITY

(75) Inventors: Michael A. Cowley, Portland, OR (US); Anthony A. McKinney, San Diego, CA (US); Gary Tollefson, Indianapolis, IN (US)

(73) Assignee: Orexigen Therapeutics, Inc., San Diego, CA (US)

( * ) Notice: Subject to any disclaimer, the term of this patent is extended or adjusted under 35 U.S.C. 154(b) by 1584 days.

This patent is subject to a terminal disclaimer.

(21) Appl. No.: 11/602,571

(22) Filed: Nov. 21, 2006

(65) Prior Publication Data

US 2007/0128298 A1 Jun. 7, 2007

Related U.S. Application Data

(60) Provisional application No. 60/738,893, filed on Nov. 22, 2005, provisional application No. 60/759,117, filed on Jan. 12, 2006.

(51) Int. Cl.

| | |
|---|---|
| ***A61K 31/137*** | (2006.01) |
| ***A61K 31/485*** | (2006.01) |
| ***A61K 31/138*** | (2006.01) |
| ***A61K 31/4525*** | (2006.01) |
| ***A61K 31/135*** | (2006.01) |
| ***A61K 45/06*** | (2006.01) |
| ***A61K 31/423*** | (2006.01) |
| ***A61K 31/7048*** | (2006.01) |
| *A61K 31/554* | (2006.01) |
| *A61K 31/5513* | (2006.01) |
| *A61K 31/551* | (2006.01) |
| *A61K 31/55* | (2006.01) |
| *A61K 31/445* | (2006.01) |
| *A61K 31/519* | (2006.01) |
| *A61K 31/5415* | (2006.01) |

(52) U.S. Cl.

CPC ............... *A61K 31/55* (2013.01); *A61K 31/551* (2013.01); *A61K 31/138* (2013.01); *A61K 31/4525* (2013.01); *A61K 31/554* (2013.01); *A61K 31/135* (2013.01); *A61K 31/5415* (2013.01); *A61K 45/06* (2013.01); *A61K 31/5513* (2013.01); *A61K 31/519* (2013.01); *A61K 31/445* (2013.01); *A61K 31/485* (2013.01); *A61K 31/423* (2013.01); *A61K 31/7048* (2013.01)

USPC .......................................... 514/282; 514/649

(58) Field of Classification Search

USPC ............ 514/220, 221, 282, 259.41, 557, 317, 514/217, 211.13, 225.8, 649; 424/722

See application file for complete search history.

(56) References Cited

U.S. PATENT DOCUMENTS

| | | | |
|---|---|---|---|
| 3,819,706 | A | 6/1974 | Mehta |
| 3,885,046 | A | 5/1975 | Mehta |
| 3,942,641 | A | 3/1976 | Segre |
| 4,089,855 | A | 5/1978 | Chatterjie et al. |
| 4,172,896 | A | 10/1979 | Uno et al. |
| 4,218,433 | A | 8/1980 | Kooichi et al. |
| 4,295,567 | A | 10/1981 | Knudsen |
| 4,483,846 | A | 11/1984 | Koide et al. |
| 4,513,006 | A | 4/1985 | Maryanoff et al. |
| 4,673,679 | A | 6/1987 | Aungst et al. |
| 4,689,332 | A | 8/1987 | McLaughlin et al. |
| 4,831,031 | A | 5/1989 | Lowe et al. |
| 4,855,306 | A | 8/1989 | Markstein et al. |
| 4,895,845 | A | 1/1990 | Seed |
| 5,000,886 | A | 3/1991 | Lawter et al. |
| 5,028,612 | A | 7/1991 | Glover |
| 5,082,864 | A | 1/1992 | Van den Oetelaar et al. |
| 5,202,128 | A | 4/1993 | Morella et al. |
| 5,213,807 | A | 5/1993 | Chemburkar et al. |
| 5,213,808 | A | 5/1993 | Bar-Shalom et al. |
| 5,283,263 | A | 2/1994 | Norden |
| 5,312,925 | A | 5/1994 | Allen et al. |
| 5,358,970 | A | 10/1994 | Ruff et al. |
| 5,364,841 | A | 11/1994 | Cooper et al. |
| 5,403,595 | A | 4/1995 | Kitchell et al. |
| 5,426,112 | A | 6/1995 | Zagon et al. |
| 5,427,798 | A | 6/1995 | Ludwig et al. |
| 5,486,362 | A | 1/1996 | Kitchell et al. |
| 5,512,593 | A | 4/1996 | Dante |
| 5,541,231 | A | 7/1996 | Ruff et al. |

(Continued)

FOREIGN PATENT DOCUMENTS

| | | |
|---|---|---|
| CA | 2317044 | 7/1999 |
| EP | 0 005 636 | 11/1979 |

(Continued)

OTHER PUBLICATIONS

Yu et al. (Diabetes Res and Clin Practice, 68S1, 2005, S54-59).*

(Continued)

*Primary Examiner* — Kendra D Carter

*Assistant Examiner* — Jason A Deck

(74) *Attorney, Agent, or Firm* — Knobbe Martens Olson & Bear LLP

(57) ABSTRACT

Methods and compositions for treating a blood glucose condition involve identifying a suitable subject and administering an effective amount of a composition that contains one or more of an opioid antagonist, an anticonvulsant, and a psychotherapeutic agent. The compositions can include insulin. In some embodiments, such methods and compositions can be used to modulate a blood glucose level. In preferred embodiments, such methods and compositions are useful for increasing a subject's sensitivity to insulin.

31 Claims, No Drawings

(56) References Cited

U.S. PATENT DOCUMENTS 5,626,874 A 5/1997 Conte et al.
5,714,519 A 2/1998 Cincotta et al.
5,716,976 A 2/1998 Bernstein
5,719,197 A 2/1998 Kanios et al.
5,731,000 A 3/1998 Ruff et al.
5,738,874 A 4/1998 Conte et al.
5,763,493 A 6/1998 Ruff et al.
5,817,665 A 10/1998 Dante
5,856,332 A 1/1999 Dante
5,866,164 A 2/1999 Kuczynski et al.
5,958,962 A 9/1999 Cook
5,977,099 A 11/1999 Nickolson
6,004,970 A 12/1999 O'Malley et al.
6,033,686 A 3/2000 Seth
6,034,091 A 3/2000 Dante
6,048,322 A 4/2000 Kushida
6,071,537 A 6/2000 Shank
6,071,918 A 6/2000 Cook
6,087,386 A 7/2000 Chen et al.
6,096,341 A 8/2000 Seth
6,110,973 A 8/2000 Young
6,120,803 A 9/2000 Wong et al.
6,143,327 A 11/2000 Seth
6,150,366 A 11/2000 Arenson et al.
6,153,223 A 11/2000 Apelian et al.
6,183,778 B1 2/2001 Conte et al.
6,191,117 B1 2/2001 Kozachuk
6,197,827 B1 3/2001 Cary
6,210,716 B1 4/2001 Chen et al.
6,238,697 B1 5/2001 Kumar et al.
6,245,766 B1 6/2001 Watsky
6,248,363 B1 6/2001 Patel et al.
6,262,049 B1 7/2001 Coffin et al.
6,274,579 B1 8/2001 Morgan et al.
6,294,192 B1 9/2001 Patel et al.
6,306,436 B1 10/2001 Chungi et al.
6,323,236 B2 11/2001 McElroy
6,342,496 B1 1/2002 Jerussi et al.
6,342,515 B1 1/2002 Masuda et al.
6,344,474 B1 2/2002 Maruani et al.
6,369,113 B2 4/2002 Young
6,383,471 B1 5/2002 Chen et al.
6,387,956 B1 5/2002 Shapira
6,420,369 B1 7/2002 Marcotte
6,437,147 B1 8/2002 Andersen et al.
6,441,038 B1 8/2002 Cook
6,451,860 B1 9/2002 Young
6,462,237 B1 10/2002 Gidwani et al.
6,500,459 B1 12/2002 Chhabra et al.
6,506,799 B1 1/2003 Dasseux
6,514,531 B1 2/2003 Alaux et al.
6,528,520 B2 * 3/2003 Clemens ...................... 514/282
6,541,478 B1 4/2003 O'Malley et al.
6,548,551 B2 4/2003 Hinz
6,569,449 B1 5/2003 Stinchcomb et al.
6,576,256 B2 6/2003 Liang et al.
6,589,553 B2 7/2003 Li et al.
6,622,036 B1 9/2003 Suffin
6,627,223 B2 9/2003 Percel et al.
6,630,165 B2 10/2003 Seroff et al.
6,638,535 B2 10/2003 Lemmens et al.
6,652,882 B1 11/2003 Odidi et al.
6,682,759 B2 1/2004 Lim et al.
6,686,337 B2 2/2004 Connor
6,706,283 B1 3/2004 Appel et al.
6,713,488 B2 3/2004 Sadee et al.
6,797,283 B1 9/2004 Edgren et al.
6,893,660 B2 5/2005 Li et al.
6,893,661 B1 5/2005 Odidi et al.
6,905,708 B2 6/2005 Li et al.
6,923,988 B2 8/2005 Patel et al.
6,926,907 B2 8/2005 Plachetka
6,995,169 B2 2/2006 Chapleo et al.
7,109,198 B2 9/2006 Gadde et al.
7,375,111 B2 5/2008 Weber et al.
7,422,110 B2 9/2008 Zanden et al.
7,425,571 B2 9/2008 Gadde et al.
7,429,580 B2 9/2008 Gadde et al.
7,462,626 B2 12/2008 Weber et al.
7,682,633 B2 3/2010 Matthews et al.
7,754,748 B2 7/2010 Gadde et al.
8,318,788 B2 11/2012 McKinney et al.
2001/0025038 A1 9/2001 Coffin et al.
2001/0046964 A1 11/2001 Percel et al.
2002/0012680 A1 1/2002 Patel et al.
2002/0019364 A1 2/2002 Renshaw
2002/0022054 A1 2/2002 Sawada et al.
2002/0025972 A1 2/2002 Hinz
2002/0037836 A1 3/2002 Henriksen
2002/0044962 A1 4/2002 Cherukuri et al.
2002/0055512 A1 5/2002 Marin et al.
2002/0090615 A1 7/2002 Rosen et al.
2002/0198227 A1 * 12/2002 Bernstein ...................... 514/282
2003/0003151 A1 1/2003 Chopra
2003/0017189 A1 1/2003 Wong et al.
2003/0035840 A1 2/2003 Li et al.
2003/0044462 A1 3/2003 Subramanian et al.
2003/0054031 A1 3/2003 Li et al.
2003/0054041 A1 3/2003 Lemmens et al.
2003/0055008 A1 3/2003 Marcotte
2003/0055038 A1 3/2003 Howard et al.
2003/0068371 A1 4/2003 Oshlack et al.
2003/0087896 A1 5/2003 Glover
2003/0091630 A1 5/2003 Louie-Helm et al.
2003/0109546 A1 6/2003 Fenton
2003/0130322 A1 7/2003 Howard
2003/0133982 A1 7/2003 Heimlich et al.
2003/0133985 A1 7/2003 Louie-Helm et al.
2003/0135056 A1 7/2003 Anderson et al.
2003/0144174 A1 7/2003 Brennan et al.
2003/0144271 A1 7/2003 Shulman
2003/0147952 A1 8/2003 Lim et al.
2003/0161874 A1 8/2003 Li et al.
2003/0198683 A1 10/2003 Li et al.
2003/0215496 A1 11/2003 Patel et al.
2004/0002462 A1 1/2004 Najarian
2004/0005368 A1 1/2004 Mann et al.
2004/0022852 A1 2/2004 Chopra
2004/0029941 A1 * 2/2004 Jennings ...................... 514/379
2004/0047908 A1 3/2004 Lemmens et al.
2004/0059241 A1 3/2004 Suffin
2004/0092504 A1 5/2004 Benja-Athon
2004/0096499 A1 5/2004 Vaya et al.
2004/0101556 A1 5/2004 Li et al.
2004/0105778 A1 6/2004 Lee et al.
2004/0106576 A1 6/2004 Jerussi et al.
2004/0115134 A1 6/2004 Merisko-Liversidge
2004/0122033 A1 6/2004 Nargund et al.
2004/0158194 A1 8/2004 Wolff et al.
2004/0185097 A1 9/2004 Kannan et al.
2004/0204472 A1 * 10/2004 Briggs et al. ................. 514/406
2004/0228915 A1 11/2004 Noack et al.
2004/0228924 A1 11/2004 Oshlack et al.
2004/0242974 A1 12/2004 Glover
2004/0254208 A1 * 12/2004 Weber et al. ................. 514/282
2004/0258757 A1 12/2004 Bosch et al.
2005/0004106 A1 1/2005 Romano
2005/0013863 A1 1/2005 Lim et al.
2005/0019385 A1 1/2005 Houze
2005/0019409 A1 1/2005 Edgren et al.
2005/0019412 A1 1/2005 Bosch et al.
2005/0026977 A1 2/2005 Jennings
2005/0026986 A1 2/2005 Maruani et al.
2005/0031691 A1 2/2005 McGurk et al.
2005/0043704 A1 2/2005 Lieberburg
2005/0043705 A1 2/2005 Lieberburg
2005/0043773 A1 2/2005 Lieberburg
2005/0063913 A1 3/2005 Pruitt et al.
2005/0096311 A1 5/2005 Suffin et al.
2005/0112198 A1 5/2005 Challapalli et al.
2005/0112211 A1 5/2005 Gervais et al.
2005/0118268 A1 6/2005 Percel et al.
2005/0137144 A1 6/2005 Gadde et al.
2005/0142195 A1 6/2005 Li et al.

(56) References Cited

U.S. PATENT DOCUMENTS

2005/0143322 A1 6/2005 Gadde et al.
2005/0147664 A1 7/2005 Liversidge et al.
2005/0154002 A1 7/2005 Crooks et al.
2005/0163840 A1 7/2005 Sawada et al.
2005/0181049 A1 8/2005 Dong et al.
2005/0181070 A1 8/2005 Gadde et al.
2005/0214368 A1 9/2005 Kawakami et al.
2005/0214371 A1 9/2005 Di Capua et al.
2005/0214372 A1 9/2005 Di Capua et al.
2005/0215552 A1 9/2005 Gadde et al.
2005/0232990 A1 10/2005 Boehm et al.
2005/0238718 A1 10/2005 Oberegger et al.
2005/0245460 A1 11/2005 Meyerson et al.
2005/0250838 A1 11/2005 Challapalli et al.
2005/0277579 A1 12/2005 Gadde et al.
2006/0009514 A1 1/2006 Gadde et al.
2006/0018933 A1 1/2006 Vaya et al.
2006/0018934 A1 1/2006 Vaya et al.
2006/0024365 A1 2/2006 Vaya et al.
2006/0058293 A1 3/2006 Weber et al.
2006/0069086 A1 3/2006 Michalow
2006/0079501 A1 4/2006 Krishnan et al.
2006/0100205 A1 5/2006 Weber et al.
2006/0122127 A1 6/2006 Rao et al.
2006/0160750 A1 7/2006 Krishnan et al.
2006/0246131 A1 11/2006 Cottinham
2006/0276412 A1 12/2006 Tollefson
2007/0078135 A1 4/2007 Yuan et al.
2007/0117827 A1 5/2007 Tollefson et al.
2007/0129283 A1 6/2007 McKinney et al.
2007/0148237 A1 6/2007 McKinney et al.
2007/0149451 A1* 6/2007 Holmes ........................... 514/12
2007/1048237 6/2007 McKinney et al.
2007/0179168 A1 8/2007 Cowley et al.
2007/0185084 A1 8/2007 McKinney et al.
2007/0270450 A1 11/2007 Weber et al.
2007/0275970 A1 11/2007 Weber et al.
2007/0281021 A1 12/2007 McKinney et al.
2008/0027487 A1 1/2008 Patel et al.
2008/0058407 A1 3/2008 Baron et al.
2008/0110792 A1 5/2008 McKinney et al.
2008/0113026 A1 5/2008 McKinney et al.
2008/0214592 A1 9/2008 Cowley et al.
2009/0018115 A1 1/2009 Gadde et al.
2009/0076108 A1 3/2009 Gadde et al.
2010/0166889 A1 7/2010 Sanfilippo
2010/0190793 A1 7/2010 Weber et al.
2011/0028505 A1 2/2011 McKinney et al.
2011/0059170 A1 3/2011 McKinney et al.
2011/0098289 A1 4/2011 Gadde et al.
2011/0144145 A1 6/2011 Tollefson
2011/0172260 A1 7/2011 Dunayevich et al.
2012/0010232 A1 1/2012 Weber et al.
2013/0177602 A1 7/2013 McKinney et al.
2013/0245055 A1 9/2013 Wright
2013/0252995 A1 9/2013 Dunayevich et al.

FOREIGN PATENT DOCUMENTS

EP 0 294 028 12/1988
EP 0294028 12/1988
EP 0 442 769 8/1991
EP 0 541 192 5/1993
EP 0541192 5/1993
EP 0 598 309 5/1994
EP 1 275 373 1/2003
EP 1 759 701 7/2007
EP 1 813 276 8/2007
RU 2214241 10/2003
WO WO 83/03197 9/1983
WO WO 90/13294 11/1990
WO WO 94/20100 9/1994
WO WO 96/09047 3/1996
WO WO 97/06786 2/1997
WO WO 97/06787 2/1997
WO WO 97/41873 11/1997
WO WO 98/00130 1/1998
WO WO 99/37305 7/1999
WO WO 99/38504 8/1999
WO WO 00/50020 8/2000
WO WO 00/51546 9/2000
WO WO 00/61139 10/2000
WO WO 00/62757 10/2000
WO WO 00/76493 12/2000
WO WO 01/01973 1/2001
WO WO 01/26641 4/2001
WO WO 01/52833 7/2001
WO WO 01/52851 7/2001
WO WO 01/58451 8/2001
WO WO 01/62257 8/2001
WO WO 01/78725 10/2001
WO WO 01/85257 11/2001
WO WO 02/09694 2/2002
WO WO 02/24214 3/2002
WO WO 02/087590 11/2002
WO WO 03/013524 2/2003
WO WO 03/013525 2/2003
WO WO 03/013479 3/2003
WO WO 03/092682 11/2003
WO WO 03/097051 11/2003
WO WO 2004/002463 1/2004
WO WO 2004/009015 1/2004
WO WO 2004/024096 A2 3/2004
WO WO 2004/052289 6/2004
WO WO 2004/054570 7/2004
WO WO 2004/054571 7/2004
WO WO 2004/071423 8/2004
WO WO 2004/091593 10/2004
WO WO 2004/096201 11/2004
WO WO 2004/100956 11/2004
WO WO 2004/100992 11/2004
WO WO 2005/089486 11/2004
WO WO 2004/110368 12/2004
WO WO 2004/110375 12/2004
WO WO 2005/000217 1/2005
WO WO 2005/077362 2/2005
WO WO 2005/032555 4/2005
WO WO 2005/049043 6/2005
WO WO 2005/070641 8/2005
WO WO 2005/079773 9/2005
WO WO 2005/089486 9/2005
WO WO 2005/110405 A1 11/2005
WO WO 2006/049941 5/2006
WO WO 2006/052542 5/2006
WO WO 2006/055854 5/2006
WO WO 2006/088748 8/2006
WO WO 2007/012064 1/2007
WO WO 2007/047351 4/2007
WO WO 2007/85637 8/2007

OTHER PUBLICATIONS

Givens et al. (J Clin Endocrinol Metab, Feb;64(2): 377-82)—1987.*
Fulghesu et al. (Obstetrics & Gynecology, 82, 2, 1993, p. 191-197).*
Insulin Resistance and Pre-Diabetes (http://diabetes.niddk.nih.gov/DM/pubs/insulinresistance/ )—2009.*
Bupropion document (Bupropion—Mayo clinic.com)—2009.*
Zonisamide document (Zonisamide—Mayo clinic.com)—2009.*
Naltrexone document (Naltrexone—Mayo clinic.com)—2009.*
Rao (Intensive Care Med, 1998).*
Baldassano, et al. 2006. Acute treatment of bipolar depression with adjunctive zonisamide: A retrospective chart review. *Bipolar Disorders*, 6:432-434.
Calabrese, et al. 2000. Letters to the Editor. Lamotrigine and Clozapine for Bipolar Disorder. *American J. of Psychiatry*, 157(9):1523.
Chengappa, et al. 2002. Changes in body weight and body mass index among psychiatric patients receiving lithium, valproate, or topiramate: An open-label, nonrandomized chart review. *Clinical Therapeutics*, 24(10):1576-1584.
Dembowski, et al. 2003. Successful antimanic treatment and mood stabilization with lamotrigine, clozapine, and valproate in a bipolar

(56) References Cited

OTHER PUBLICATIONS patient after lithium-induced cerebellar deterioration. *Pharmacopsychiatry*, 36:83-86.

Dursen, et al. 1999. Clozapine plus lamotrigine in treatment-resistant schizophrenia. *Arch. Gen. Psychiatry*, 56:950-951.

Dursun, et al. 2001a. Augmenting antipsychotic treatment with lamotrigine or topiramate in patients with treatment-resistant schizophrenia: A naturalistic case-series outcome study. *Journal of Psychopharmacology*, 15(4):297-301.

Dursun, et al. 2001b. Psychopharmacology for the clinician psychopharmacologie pratiqu. *Journal of Psychiatry & Neuroscience*, 26(2):168.

Ferre, et al. 1996a. Evidence from transgenic mice that glucokinase is rate limiting for glucose utilization in the liver. *The FASEB Journal*, 10:1213-1218.

Ferre, et al. 1996b. Correction of diabetic alterations by glucokinase. *Proc. Natl. Acad. Sci. USA*, 93:7225-7230.

Gadde, et al. 2001. Bupropion for weight loss: An investigation of efficacy and tolerability in overweight and obese women. *Obesity Research*, 9(9):544-551.

Gadde, et al. 2003. Zonisamide for weight loss in obese adults: A randomized controlled trial. *JAMA*, 289(14):1820-1825.

Ginsberg, et al. 2000. Effects of mood stabilizers on weight. *Primary Psychiatry*, 7(5):49-58.

Gordon, et al. 1999. Mood stablization and weight loss with topiramate. *American Journal of Psychiatry*, 156(6):968-969.

Kimura, et al. 1992. Pharmacokinetic interaction of zonisamide in rats. Effect of other antiepileptics on zonisamide. *J. Phannacobio-Dyn.*, 15:631-639.

Kirov, et al. 2005. Add-on topiramate reduces weight in overweight patients with affective disorders: A clinical case series. *BMC Psychiatry*, 5:19, 8 pp.

Lessig, et al. 2001. Topiramate for reversing atypical antipsychotic weight gain. *J. Am. Acad. Child Adolesc. Psychiatry*, 40(12):1364.

Levy, et al. 2002. Topiramate produced weight loss following olanzapine-induced weight gain in schizophrenia. *The Journal of Clinical Psychiatry*, 63(11):1045.

Matsuura, M. 2000. Indication for anterior temporal lobectomy in patients with temporal lobe epilepsy and psychopathology. *Epilepsia*, 41(Suppl. 9):39-42.

National Institute of Diabetes and Digestive and Kidney Diseases. National Diabetes Statistics fact sheet: general information and national estimates on diabetes in the United States, 2003. Bethesda, MD: U.S. Department of Health and Human Services, National Institutes of Health, 2003. Rev. ed. Bethesda, MD: U.S. Department of Health and Human Services, National Institutes of Health, 2004. NIH Publication No. 05-3892, Dec. 2004. Retrieved Jan. 15, 2008, from http://web.archive.org/web/20050228083404/diabetes.niddk.nih.gov/dm/pubs/statistics/.

Navarro, et al. 2001. Topiramate for clozapine-induced seizures. *Am. J. Psychiatry*, 158(6):968-969.

Niswender, et al. 1997. Effects of increased glucokinase gene copy number on glucose homeostatis and hepatic glucose metabolism. *The Journal of Biological Chemistry*, 272(36):22570-22575.

Reaven, G. M. 1995. Pathophysiology of insulin resistance in human disease. *Physiological Reviews*, 75(3):473-486.

Saba, et al. 2002. Lamotrigine-clozapine combination in refractory schizophrenia: Three cases. *The Journal of Neuropsychiatry and Clinical Neurosciences*, 14:1:86.

Tollefson, et al. 1997. Olanzapine versus haloperidol in the treatment of schizophrenia and schizoaffective and schizophreniform disorders: Results of an international collaborative trial. *Am. J. Psychiatry*, 154(4):457-465.

Van Schaftingen, et al. 1992. The regulatory protein of liver glucokinase. *Advan. Enzyme Regul.*, 32:133-148.

Vieta, et al. 2003. 1-year follow-up of patients treated with risperidone and topiramate for a manic episode. *J. Clin. Psychiatry*, 64(7):834-839.

Vieta, et al.2004. Effects on weight and outcome of long-term olanzapine-topiramate combination treatment in bipolar disorder. *Journal of Clinical Psychopharmacology*, 24(4):374-378.

Wang, et al. 2002. Gabapentin augmentation therapy in bipolar depression. *Bipolar Disorders*, 4:296-301.

Invitation to Pay Additional Fees dated Jul. 24, 2007, from International Application No. PCT/US2006/044966 filed Nov. 20, 2006, including partial International Search and cited non-patent references.

International Search Report and Written Opinion dated Nov. 19, 2007, from International Application No. PCT/US2006/044966 filed Nov. 20, 2006.

Clark et al: "Diabetes mellitus associated with atypical anti-psychotic medications," Diabetes Technology & Therapeutics, vol. 5, No. 4, 2003, pp. 669-683.

Fontela et al: "Blocking effect of naloxone, dihydroergotamine and adrenalectomy in lithium-induced hyperglycaemia and glucose intolerance in the rat," ACTA Endocrinologica, vol. 111, No. 3, Mar. 1986, pp. 342-348.

Gerra et al: "Effects of olanzapine on aggressiveness in heroin dependent patients," Progress in Neuro-psychopharmacology & Biological Psychiatry, Oxford, vol. 30, No. 7, Sep. 30, 2006, pp. 1291-1298.

Islam et al: "Naltrexone, Serotonin Receptor Subtype Antagonists, and Carbohydrate Intake in Rats," Pharmacology Biochemistry and Behavior, vol. 48, No. 1, Jan. 1, 1994, pp. 193-201.

Najim et al: "Role of endorphins in benzodiazepine-induced hyperglycaemia in mice," Pharmacology Biochemistry and Behavior, vol. 46, No. 4, Dec. 1, 1993, pp. 995-997.

O'Byrne et al: "Effects of drugs on glucose tolerance in non-insulin-dependent diabetes (Part II)," Drugs, Adis International Ltd., vol. 40, No. 2, Jan. 1, 1990, p. 205.

Paile-Hyvarinen et al: "Quality of life and metabolic status in mildly depressed women with type 2 diabetes treated with paroxetine: A single-blind randomized placebo controlled trial," BMC Family Practice, vol. 4, No. 1, May 14, 2003, p. 7.

Scheen et al: "Diabete sucre iatrogene: L'exemple des anti-psychotiques atypiques," Revue Medicale de Liege, vol. 60, No. 5-6, May 1, 2005, pp. 455-460.

Ackerman et al. 1998. Clinical characteristics of response to fluoxetine treatment of obsessive-compulsive disorder. Journal of Clinical Psychopharmacology, 18(3):185-192.

Altman et al. (2005) Standard Deviations and Standard Errors, BMJ, 331:903.

Anderson et al. (2002) Bupropion SR enhances weight loss, Obesity R., 10(7):633-641.

Appolinario et al. (2004) Pharmacological Approaches in the Treatment of Binge Eating Disorder, Current Drug Targets, 5:301-307.

Aronne et al. (2003) Weight gain in the treatment of mood disorders, J. Clin Psychiatry, 64(suppl 9).

Asconape, 2002, Some Common Issues in the Use of Antiepileptic Drugs, Seminars in Neurology; 22(1):27-39.

Astrup et al. (Mar. 1991) Thermogenic Synergism Between Ephedrine and Caffeine in Healthy Volunteers: A Double-Blind, Placebo-Controlled Study, Metabolism, 40(3):323-329.

Atkinson (2003) Clinical Guidelines on the identification, Evaluation, and pharmacologic treatment of obesity in Adults, Online, 07-25, URL:http://www.endotext.org.obesity/obesity15b/obesity15b.htm.

Atkinson et al. (Oct. 1985) Effects of long-term therapy with naltrexone on body weight in obesity, Clinical Pharmacology & Therapeutics, 38:419-422.

Ayala (2000) Weight Loss Associated With the Administration of Zonisamide, AES Proceedings, Epilepsia 41(Suppl. 7) :99—No. 2.041.

Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.

Barr et al. 1993. The serotonin hypothesis of obsessive compulsive disorder. International Clinical Psychopharmacology, 8(2):79-82.

Bastani et al. 1991. Serotonin uptake and imipramine binding in the blood platelets of obsessive-compulsive disorder patients. Biol. Psychiatry, 30:131-139.

(56) References Cited

OTHER PUBLICATIONS

Beelen et al. (2001) Asymptomatic QTC prolongation associated with queitiapine fumarate overdose in a patient being treated with risperidone, Human & Experimental Toxicology 20:215-219.
Benjamin et al. 1993. Naltrexone and fluoxetine in Prader-Willi syndrome. J. Am. Acad. Child Adolesc. Psychiatry, 32(4):870-873.
Bergeron et al. 2002. Sertraline and fluoxetine treatment of obsessive-compulsive disorder: Results of a double-blind, 6-month treatment study. Journal of Clinical Psychopharmacology, 22(2):148-154.
Berke et al. (Jul. 15, 2000) Medical Management of Obesity, American Academy of Family Physicians, 62(2):419-26 Abstract.
Billett et al. 1997. Obsessive compulsive disorder, response to serotonin reuptake inhibitors and the serotonin transporter gene. Molecular Psychiatry, 2:403-406.
Blanchard et al. (2003) Pancreatitis Treated with Didanosine and Tenofabir Disoproxil Fumarate Clinical Infectious Diseases, 37:57-62.
Broocks et al. 1998. Higher prevalence of obsessive-compulsive symptoms in patients with blepharospasm than in patients with hemifacial spasm. Am. J. Psychiatry, 155:555-557.
Carlsen et al. (Jan. 1998) Evidence for dissociation of insulin-and weight-reducing effects of metformin in non-diabetic male patients with coronary heart disease, Diabetes Research and Clinical Practice Amersterdam, 39(1):47-54.
Carpenter et al. (Jan. 1, 1999) Mirtazapine Augmentation in the Treatment of Refractory Depression, J Clin Psychiatry, 60:1.
Carrion, 1995. Naltrexone for the treatment of trichotillomania: A case report. J. Clin. Psychopharmacol., 15(6):444-445.
Carroll (2003) Medicinal Chemistry Division Award Address: Monoamine Transporters and Opioid Receptors. Targets for Addiction Therapy, J. Med. Chem; 46(10)1775-1794.
Carter et al. 2003. Pharmacologic treatment of binge-eating disorder. Primary Psychiatry, 10(10)31-36.
Cash et al. (2000) Attitudes about antidepressants: Influence of information about weight-related side effects, Perceptual and Motor Skills, 90:453-456.
Casner et al. 1996. Naltrexone and self-injurious behavior: A retrospective population study. Journal of Clinical Psychopharmacology, 16(5):389-394.
Chen et al. (Jan. 2004) Synergistic Effects of Cannabiniod inverse agonist AM251 and opioid antagonist namefene on food intake, Brain Res, 999:22-230.
Ching, Mar. 1980, Influence of diphenylhydantoin upon oral glucose tolerance test in obesity, Chinese Medical Journal, 27(1):432-439.
Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
Colosimo, et al. 1999. Motor fluctuations in Parkinson's disease: Pathophysiology and treatment. European Journal of Neurology, 6:1-21.
Cone et al. (2001) The arcuate nucleus as a conduit for diverse signals relevant to energy homeostasis, Int'l Journal of Obesity, 25(5):S63-S67.
Croft et al. (Apr. 2002) Effect on body weight of bupropion sustained-release in patients with major depression treated for 52 weeks, Clinical Therapeutics 24(4):662-672.
Dechant et al. (1991) Drugs, 41:225-253.
Deshmukh et al. (Jul. 2003) Managing weight gain as a side effect of antidepressant therapy, Cleveland Clinic Journal of Medicine, vol. 70.
DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dwyer et al., 2002, Psychoactive drugs affect glucose transport and the regulation of glucose metabolism, International Review of Neurobiology, 51:503-530.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain β-naltrexamine. Evidence for bridging between proximal recognition sites, J. Med. Chem., 25:847-849.
Erfuth et al. (Mar. 2002) Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.
Faught et al. (2001) Randomized Controlled Trial of Zonisamide for the Treatment of Refractory Partial-Onset Seizures., Neurology; 57(10):1774-1779.
Fava, Maurizio (2000) Weight Gain and Antidepressants. J Clin Psychiatry; 61(suppl 11):37-41.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rate, Acta Endocrinologica, 111(3):342348 (abstract).
Fukagawa et al. (Nov. 2001) Monoaminergic anorectic agents, Nippon Yikurigaku Zasshi, 118(5):303-8, 2001 Abstract.
Fuller et al. (1989) Fluoxetine: A Serotonergic Appetite Suppressant Drug, Drug Development Research, 17(1):1-15.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. (2003) Zonisamide enhances weight loss in patients with obesity. Inpharma; 1383/84:9.
Gadde et al., 2002, Randomized controlled trial of zonisamide for treating obesity, Epilepsia 43 Suppl. 7:218 (abstract).
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al. (1996) $^{123}$I-labeled AM251: a radioiodinated ligand which binds in vivo to mouse brain cannabinoid $CB_1$ receptors. European Journal of Pharmacology; 307:331-338.

(56) References Cited

OTHER PUBLICATIONS

Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-823.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Glass et al. (1999) Opioids and food intake: distributed functional neural pathways? Neuropeptides; 33(5):360-368.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman et al. 1989. The Yale-Brown obsessive compulsive scale. Arch. Gen. Psychiatry, 46:1006-1011.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2000) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Non-prescription Medications for the Treatment of Obesity, Obesity Research, 7(4):370-78.
Greist et al. (Apr. 1995) Double-blind Parallel Comparison of Three Dosages of Sertraline and Placebo in Outpatients With Obsessive-compulsive Disorder, Arch Gen Psychiatry, 52:289-295.
Grunenthal, Neo-Eunomin Gebrauschsinformation, Neunomin Prescription Information, Feb. 2004, pp. 1-2.
Hahn et al. (1985) Irreversible opiate agonists and antagonists. III. Phenylhydrazone derivatives of naloxone and oxymorphone. J. Pharm. Exper. Therapeutics; 235:846-850.
Hamidi et al. 2007. Naltrexone in obsessive-compulsive disorder: An open- label trial. Iranian Journal of Psychiatry and Behavioral Sciences, 1(1):16-21.
Harrison's Principles of Internal Medicine, Braunwald et al., The epilepsies and convulsive disorders, Eleventh Edition, McGraw-Hill Book Company, pp. 1921-1930 (1987).
Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.
Hollander et al. 1991. Effects of chronic fluoxetine treatment on behavioral and neuroendocrine responses to meta-chlorophenylpiperazine in obsessive-compulsive disorder. Psychiatry Research, 36:1-17.
Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.
Islam et al., 1994, Naltrexone, Serotonin Receptor Subtype Antagonists, and Carbohydrate Intake in Rats, Pharmacology Biochemistry and Behavior, 48(1):193-201.
Jain et al. (Oct. 2002) Bupropin SR vs. Placebo for Weight Loss in Obese Patients with Depressive Symptoms, Obesity Research, 10:1049-56.
Jallon et al. (2001) Bodyweight gain and anticonvulsants: a comparative review. Drug Safety; 24(13):969-978.
Japanese Journal of Clinical Psychiatry (1987 16(1):123-132), and English-language version of Japanese Office Action citing the same (dated Oct. 28, 2008).
Kanba et al. (1994) The first open study of zonisamide, a novel anticonvulsant, shows efficacy in mania. Progress in Neuro-Psychopharmacology and Biological Psychiatry; 18(4):707-715.
Kim et al. 1990. Open fixed dose trial of fluoxetine in the treatment of obsessive compulsive disorder. Drug Development Research, 19:315-319.
Kiptoo et al. (2006) Enhancement of Transdermal delivery or 6-B-naltrexol via a codrug linked to hydroxyburpropion, Journal of Controlled Release 113:137-145.
Kirkham et al. (2001) Synergistic effects of opioid and cannabinoid antagonists on food intake. Psychopharmacology; 153:267-270.
Klok et al., 2002, Cholesteryl-(l-lactic acid)n. building blocks for self-assembling biomaterials, Macromolecules, 35:746-759.
Kolb et al. (1985) Synthesis and Pharmacological Characterization of Fluorescent Opioid Receptor Probes. A. Pharmaceutical Res, 2(6):266-271.
Korner et al. (2003) The emerging science of body weight regulation and its impact on obesity treatment, J. Clin. Invest. 111(5):565-570.
Kossard, et al. 2006. Defining urticarial dermatitis: A subset of dermal hypersensitivity reaction pattern. Arch. Dermatol., 142:29-34.
Krauss et al. 1997. Tics secondary to craniocerebral trauma, Movement Disorders, 12(5):776-782.
Krupitsky et al. 2006. Naltrexone with or without fluoxetine for preventing relapse to heroin addiction in St. Petersburg, Russia. Journal of Substance Abuse Treatment, 31:319-328.
Kushner et al. (Mar. 2002) Obesity pharmacology: past, present, and future, Current Opinion in Gastroenterology, pp. 213-220.
Landabaso et al. 1998. A randomized trial of adding fluoxetine to a naltrexone treatment programme for heroin addicts. Addiction, 93(5):739-744.
Le Bourdonnec et al., 2002, Reporter affinity labels: an o-phthalaldehyde derivative of β-naltrexamine as a fluorogenic ligand for opioid receptors, J. Med. Chem., 43(13):2489-2492.
Leppik (Dec. 2004) Zonisamide: chemistry, mechanism of action, and pharmacokinetics, Seizure, 13(Suppl 1):S5-9; discussion S10.
Leppik et al. (1993) Efficacy and safety of zonisamide: results of a multicenter study. Epilepsy Research; 14:165-173.
Lesch et al. 1991. Long-term fluoxetine treatment decreases 5-HT1A receptor responsivity in obsessive-compulsive disorder. Psychopharmacology, 105:415-420.
Levy et al. 1985. Utility of free level monitoring of antiepileptic drugs. Epilepsia, 26(3):199-205.
Lin et al. 2000. Development of high fat diet-induced obesity and leptin resistance in C57B1/6J mice. International Journal of Obesity, 24:639-646.
López-Ibor, Jr. et al. 1996. Double-blind comparison of fluoxetine versus clomipramine in the treatment of obsessive compulsive disorder. European Neuropsychopharmacology, 6:111-118.
Malcolm et al. (Jun. 1985) A Controlled Trial of Naltrexone in Obese Humans, International Journal of Obesity, 9:347-353.
Malhotra et al. (2002) Medical Management of Obesity Associated With Mental Disorders, Journal of Clinical Psychiatry, 63(suppl 4):24-32.
McDougle et al. (Aug. 2000) A double-blind, placebo-controlled study of risperidone addition in serotonin reuptake inhibitor-refractory obsessive-compulsive disorder, Archive of General Psychiatry, 57(8):794-801.
McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.

(56) References Cited

OTHER PUBLICATIONS

McLaughin et al. (2003) The cannabinoid CB1 antagonists SR 141716A and AM 251 suppress food intake and food-reinforced behavior in a variety of tasks in rats. Behavioral Pharmacology; 14:583:588.

Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.

Millet et al. 1999. Obsessive-compulsive disorder: Evaluation of clinical and biological circadian parameters during fluoxetine treatment. Psychopharmacology, 146:268-274.

Mitchell et al. (1987) High-Dose Naltrexone Therapy and Dietary Counseling for Obesity, Biological Psychiatry, 22:35-42.

Monteleone et al. 1995. Plasma melatonin and cortisol cirdadian patterns in patients with obsessive-compulsive disorder before and after fluoxetine treatment. Psychoneuroendocrinology, 20(7):763-770.

Morris, III (Dec. 3, 2000) The Effect of Zonisamide Administration on Patient Weight, A Scientific Exhibit at the American Epilepsy Society Annual Meeting, Los Angeles, California.

Must et al. (Oct. 27, 1999) The disease burden associated with overweight and obesity, JAMA, 282(16):1523-1529.

Najim et al., Dec. 1, 1993, Role of endorphins in benzodiazepine-induced hyperglycaemia in mice, Pharmacology Biochemistry and Behavior, 46(4):995-997.

Nash et al., Jul. 1, 2004, Anxiety disorders, Medicine, 32(7):17-21.

NDA 20-711, Approval Letter of Application No. NDA 20-711, Department of Health and Human Services, May 14, 1997, 3 pp.

NDA20-789, Zonegran (zonisamide) Capsules 100 mg, FDA Approved Labeling Text, p. 1-24 (Mar. 27, 2000).

Neumeister et al. 1999. Addition of naltrexone to fluoxetine in the treatment of binge eating disorder. Am. J. Psychiatry, 156(5):797.

Ninan et al., 1992, An improved synthesis of noroxymorphont, Tetrahedron., 48(32):6709-6716.

Note for guidance on stability testing of existing active substances and related finished product, Committee for Proprietary Medicinal Products (CPMP), Apr. 22, 1998, 9 pp.

Novi et al. (Apr.-Jun. 1990) The role of opioid antagonists in the treatment of obesity. Results of a clinical trial with naltrexone, Minerva Endocrinol. 15(2):121-3, Abstract.

O'Byrne et al., Jan. 1, 1990, Effects of drugs on glucose tolerance in non-insulin-dependent diabetes (part II), Drugs, Adis International Ltd., 40(2):204-219.

Okada et al. (1992) Effects of zonisamide on extracellular levels of monoamine and its metabolite, and on Ca2+ dependent dopamine release Epilepsy Research, 13:113-119.

Okada et al. (1995) Effects of zonisamide on dopaminergic system, Epilepsy Research, 22:198-205.

Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.

Olszewski et al. (Jun. 13, 2001) Evidence of Interactions Between Melanocortin and Opioid Systems in Regulation of Feeding, Neuroreort, 12(8):1727-1730.

Oommen et al. (1999) Zonisamide: A new antiepileptic drug. Clinical Neuropharmacology, 22(4):192-200.

Ortho-Novum Tablets and Modicon Tablets Prescribing Information, Apr. 2002, 8 pp.

Otake et al. (May 15, 2005) Association of visceral fat accumulation and plasma adiponectin and colorectal ademona: evidence for participation of insulin resistance, Clinical Cancer Research 11:3642-3646.

Ovadia, Oct. 1999, A Novel Twist on Binge Eating Treatment, Psychiatric Dispatches in Primary Psychiatry; 6(10):24-29.

Paar et al., 2002, Bivalent ligands with rigid double-stranded Dna spacers reveal structural constraints on signaling by FcϵRI, J. Immunol., 169:856-864.

Paile-Hyvarinen et al., Mar. 14, 2003, Quality of life and metabolic status in mildly depressed women with type 2 diabetes treated with paroxetine: a single blind randomised placebo controlled trial, BMC Family Practive, Biomed Central, 4(1), 6 pp.

Pasternak et al. (1980) Long-acting opiate agonists and antagonists: 14-hydroxydihydromorphinone hydrazones, Med. Chem, 23:674-676.

Pavuluri et al. (2002) Topiramate Plus Risperidone for Controlling Weight Gain and Symptoms in Preschool Mania, Journal of Child and Adolescent Psychopharmacology, 12(3):271-273.

Penn et al., 2003, Pharmacotherapy of obesity in the near term, Current Opinion in Endocrinology and Diabetes, 18(2):311-316.

Portoghese et al., 1982, Opioid agonist and antagonist bivalent ligands as receptor probes, Life Sciences, 31:1283-1286.

Portoghese et al., 1986, Opioid agonist and antagonist bivalent ligands. The relationship between spacer length and selectivity at multiple opioid receptors, J. Med. Chem., 29:1855-1861.

Portoghese et al., 1986, Synthesis and Opioid antagonist potencies of naltrexamine bivalent ligands with conformationally restricted spacers J. Med. Chem., 29:1650-1653.

Portoghese, 1992, The role of concepts in structure-activity relationship studies of opioid ligands, J. Med. Chem., 35:1927-1937.

Potter et al., 1997, Sustained Weight Loss Associated with 12-month topiramate Therapy, Epilepsia, Raven Press Ltd. NewYork, 38(Suppl 8):97.

Reents et al. (1988) Nalozone and naltrexone, Chest, 93(1):217-219.

Remington's Pharmaceutical Sciences. $18^{th}$ Edition; Easton, PA: Mack Publishing Co. (1990).

Reneric et al. (Nov. 1998) Opioid Receptor Antagonists in Psychiatry, CNS Drugs, 10(5):365-377.

Rezvani et al. 2000. Combination pharmacotherapy: a mixture of small doses of naltrexone, fluoxetine, and thyrotropin-releasing hormone analogue reduces alcohol intake in three strains of alcohol-preferring rats. Alcohol & Alcoholism, 35(1):76-83.

Romano et al. 2001. Long-term treatment of obsessive-compulsive disorder after an acute response: A comparison of fluoxetine versus placebo. Journal of Clinical Psychopharmacology, 21(1):46-52.

Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.

Rowland et al. (2001) Effects of the cannabinoid receptor antagonist SR 141716, alone and in combination with dexfenfluramine or naloxone, on food intake in rats. Psychopharmacology; 159:111-116.

Sackellares et al. (1985) Pilot study of zonisamide (1,2-benzisoxazole-3-methanesulfonamide) in patients with refractory partial seizures. Epilepsia, 26(3):206-211.

Saper et al. (2002) The need to feed: Homeostatic and hedonic control of eating, Neuron, 36:199-211.

Sashiwa et al., 2000, Chemical modification of chitosan. 3. Hyperbranched chitosan-sialic acid dendrimer hybrid with tetraethylene glycol spacer, Macromolecules, 33:6913-6915.

Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.

Scheen et al., May 1, 2005, Diabete sucre iatrogene: l'exemple des anti-phsychogiques atypiques, Revue Medicale de Liege, 60(5-6):455-460.

Schimmel et al., 1974, Inhibition by diphenylhydantoin of the diabetogenic action of streptozocin, Horm. Metab. Res. 6:475-477.

Schmidhammer et al. (1994) Mixed Azines of Naloxone with Dihydromorphinone Derivatives. A. Helv. Chim. Acta; 77:999.

Schmidt et al. (1993) Zonisamide for add-on treatment of refractory partial epilepsy: a European double-blind trial. Epilepsy Research; 15:67-73.

Shapira et al. (2000) Treatment of Binge-Eating Disorder with Topiramate: A Clinical Case Series. J. Clin. Psychiatry; 61(5):368-371.

Shapira et al. 2004. A double-blind, placebo-controlled trial of olanzapine addition in fluoxetine-refractory obsessive-compulsive disorder. Biol. Psychiatry, 550:553-555.

(56) References Cited

OTHER PUBLICATIONS

Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Sitsen et al., 2001, Drug-drug interaction studies with mirtazapine and carbamazepine in healthy male subjects, European Journal of Drug Metabolism and Pharmacokinetics, 26(1-2):109-121.
Sleep Disorders, in Diagnostic and Statistical Manual of Mental Disorders, 4th Edition, American Psychiatric Association, p. 583-595 (2000).
Sneer et al., Protective effect of diphenylhydantoin on the diabetes-inducing effect of alioxan, database accession No. 1980:34024.
Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al., 1991, Use of hydrophilic diamines for bridging of two opioid peptide pharmacophores, Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tutka et al., 2004, Convulsant and anticonvulsant effects of bupropion in mice, European Journal of Pharmacology, 499:117-120.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Walker et al. (1988) Chronic Toxicity of the Anticonvulsant Zonisamide in Beagle Dogs, Fundamental and Applied Toxicology 11:333-342.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=5231 8&ext=htm, 1 pp.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Easting Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonegran.TM. (zonisamide) capsules, FDA Approved Labeling Text, Mar. 27, 2000, 24 pp.
Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.
Atlantis et al., Oct. 6, 2009, Obesity and depression or anxiety, BMJ 2009:339:B3868.
Bays et al., Aug. 1, 2007, Adiposopathy: treating pathogenic adipose tissue to reduce cardiovascular disease risk, Current Treatment Options in Cardiovascular Medicine, 9(4):259-271.
Casado et al., Apr. 2003, Sibutramine decreases body weight gain and increases energy expenditure in obese Zucker rats without changes in NPY and orexins, Nutr Neurosci, 6(2):103-111 (abstract).
Chen et al., 2005, Combination treatment of clozapine and topiramate in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
Cunningham, May 1963, Diethylpropion in the treatment of obesity, The Journal of the College of General Practitioner, 6(2):347-349.

(56) References Cited

OTHER PUBLICATIONS

Cuparencu et al., 1993, Effects of some benzodiazepines on glycemia in albino rats, Romanian Journal of Physiology, 30(1-2):7-15 (abstract).
Durgin et al., 2005, Pharmaceutical Practice for Technicians, 3rd Edition, Thomson Delmar Learning, p. 174.
Fujioka et al., Jan. 1987, Contribution of intra-abdominal fat accumulation to the impairment of glucose and lipid metabolism in human obesity, Metabolism, 36(1):54-59.
Gormally et al., 1982, The assessment of binge eating severity among obese persons, Addict Behav, 7(1):47-55.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 2006, Bupropion and naltrexone for the treatment of obesity, Diabetes: Abstract Book: 66th Scientific Sessions, 55(Supplement 1):A394.
Greenway et al., Jun. 2006, Bupropion and naltrexone for the treatment of obesity, poster, 1 pg.
Hagan et al., Dec. 1997, Combined naloxone and fluoxetine on deprivation-induced binge eating of palatable foods in rats, Pharmacol Biochem Behav, 58(4):1103-1107.
Halpern et al., Jul. 27, 2010, Combinations of drugs in the treatment of obesity, Pharmaceuticals, 3:2398-2415.
Janssen et al., 1999, Effects of sex on the change in visceral, subcutaneous adipose tissue and skeletal muscle in response to weight loss, International Journal of Obesity, 23, pp. 1035-1046.
Jones et al., 2003, Effect of naltrexone on food intake and body weight in Syrian hamsters depends on metabolic status, Physiology & Behavior 28:67-72.
Kelly et al., 2006, Adjunct divalproex or lithium to clozapine in treatment-resistant schizophrenia, Psychiatric Quarterly, 77(1):81-94.
Kivimaki et al., Common mental disorder and obesity—insight from four repeat measures over 19 years: prospective Whitehall II cohort study, BMJ 2009; 339:b3765.
Kristeller et al., Jan. 12, 1999, An exploratory study of a meditation-based intervention for binge eating disorder, J. Health Psychol, 4(3):357-363.
Kuk et al., 2006, Visceral fat is an independent predictor of all-cause mortality in men, Obesity, 14(2):336-341.
Lowry, Feb. 2008, Study: bupropion-naltrexone combo best for weight loss, Clinical Psychiatric News, 1 pp.
McLaughlin et al., 1983, Nalmefene decreases meal size, food and water intake and weight gain in Zucker rats, Pharmacology Biochemistry and Behavior, 19(2):235-240 (abstract).
National Institutes of Health, Apr. 18, 2008, Efficacy and safety study of combination therapy to treat uncomplicated obesity, http://clinicaltrials.gov/show/NCT00364871, 5 pp.
NDA 20-789/S-005 ZONEGRAN (zonisamide) Capsules 100 mg, FDA Approved Labeling Text dated Oct. 7, 2002, 2 pp.
Padwal, Oct. 6, 2009, Contrave, a bupropion and naltrexone combination therapy for the potential treatment of obesity, Curr. Opin. Investig. Drugs, 10(10):1117-1125 (abstract).
Pandit, 2007, Introduction to the Pharmaceutical Sciences, 1st Ed., Lippincott Williams & Wilkins, Baltimore, MD, p. 154.
Shuman et al., Jun. 1986, Abnormal body fat distribution detected by computed tomography in diabetic men, Investigative Radiology, 21(6):483-487.
Stansfeld et al., Aug. 1992, Social class and minor psychiatric disorder in British civil servants: a validated screening survey using the General Health Questionnaire, Psychological Medicine, 22:739-749.
Tavakoli et al., Jul. 2003, Diabetic ketoacidosis in a patient with olanzapine, valproic acid, and venlafaxine, Southern Medical Journal, 96(7):729-730.
Turnbull et al., Jan. 1985, The effect of valproate on blood metabolite concentrations in spontaneously diabetic, ketoacidotic, bb/e wistar rats, Diabetes Research 2(1):45-48.
Van Gaal et al., Aug. 1998 , Sibutramine and fat distribution: is there a role for pharmacotherapy in abdominal/visceral fat reduction?, Int J Obes Relat Metab Disord, Suppl 1:S38-40; discussion S41-2 (abstract).
Wadden et al., Jan. 2011, Weight loss with naltrexone SR/bupropion SR combination therapy as an adjunct to behavior modification: the COR-BMOD trial, Obesity, 19(1):110-120.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.

* cited by examiner

COMPOSITIONS AND METHODS FOR INCREASING INSULIN SENSITIVITY

RELATED APPLICATION INFORMATION

This application claims priority to U.S. Provisional Patent Application Ser. Nos. 60/738,893, filed Nov. 22, 2005, and 60/759,117, filed Jan. 12, 2006, both of which are hereby incorporated by reference in their entireties.

BACKGROUND OF THE INVENTION

1. Field of the Invention

The present invention is in the field of pharmaceutical compositions and methods for the treatment of insulin related disorders in individuals.

2. Description of the Related Art

Diabetes is a chronic disease that has no cure. Currently, about 18.2 million people or 6.3% of the population in the United States have diabetes. While roughly 13 million have been diagnosed, it is estimated that 5.2 million people are not aware that they have the disease. As the sixth leading cause of death by disease in 2000, diabetes is costing the U.S. health care system an estimated $132 billion annually. See National Diabetes Information Clearinghouse, NIH Publication No. 04-3892, November 2003. More serious than the economic costs associated with diabetes is the decrease in the quality of life, serious health complications/consequences, and deaths associated with diabetes.

Diabetes is a group of diseases characterized by high blood glucose levels, which result from defects in insulin production, insulin action, or both. Because diabetes can remain undiagnosed for years, many people become aware that they have diabetes only after the development of one of its life-threatening complications. It is well-accepted that both genetics and environmental factors, such as obesity and lack of exercise, are important factors in the onset of diabetes.

One group of diabetes, Type 1 (or insulin-dependent diabetes mellitus or juvenile-onset diabetes), develops when the body's immune system destroys pancreatic cells that make the hormone insulin, which regulates blood glucose levels. Type 1 diabetes usually occurs in children and young adults, although disease onset can occur at any age. Type 1 diabetes accounts for about 5 to 10 percent of all diagnosed cases of diabetes. Risk factors for Type 1 diabetes include autoimmune, genetic, and environmental factors. Individuals diagnosed with Type 1 diabetes require daily delivery of insulin via injections or pumps.

Another group of diabetes, Type 2 (or Type II) diabetes (non-insulin-dependent diabetes mellitus (NIDDM) or adult-onset diabetes), is a metabolic disorder involving dysregulation of glucose metabolism and insulin resistance, which can result in long-term complications involving the eyes, kidneys, nerves, and blood vessels. Type 2 diabetes results from the body's inability to make either sufficient insulin (abnormal insulin secretion) or its inability to effectively use insulin (resistance to insulin action in target organs and tissues). This disease usually begins as insulin resistance, a disorder in which the cells do not use insulin properly, and as the need for insulin rises, the pancreas gradually loses its ability to produce insulin. Patients suffering from Type 2 diabetes have a relative insulin deficiency. That is, in these patients, plasma insulin levels are normal to high in absolute terms, although they are lower than predicted for the level of plasma glucose that is present. Type 2 diabetes is the most common form of the disease accounting for 90-95% of diabetes. Type 2 diabetes is nearing epidemic proportions, due to an increased number of older Americans and a greater prevalence of obesity and a sedentary lifestyle.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro- and macro-vascular complications can lead to blindness, end-stage renal disease, limb amputation and myocardial infarction Gestational diabetes refers to a form of glucose intolerance that is diagnosed in pregnant women. During pregnancy, gestational diabetes requires treatment to normalize maternal blood glucose levels to avoid complications in the infant. A percentage (5-10 percent) of women with gestational diabetes have Type 2 diabetes after pregnancy. Women who have had gestational diabetes also have a 20-50 percent chance of developing diabetes in the next 5-10 years.

Many pharmaceutical compositions and methods have been proposed to treat and/or cure diabetes. For example, one approach to reducing hyperglycemia in diabetes involves increasing liver glucokinase (GK) activity (Van Schaftingen, E. et al., Adv. Enzyme Regul. 32:133-148, 1992). Studies involving transgenic diabetic mice have shown that increased GK copy number results in increased hepatic glucose metabolism and decreased plasma glucose levels (Ferre, T. et al., Proc. Natl. Acad. Sci. USA, 93:7225-7230, 1996; FASEB J., 10:1213-1218, 1996; Niswender, K. D. et al., J. Biol. Chem., 272:22570-22575, 1997), demonstrating that increasing liver GK may be effective in reducing hyperglycemia in diabetes.

U.S. Pat. No. 5,714,519 (hereinafter the '519 patent) discloses methods for controlling either hyperinsulinemia or insulin resistance by administering panthethine (see claims 1-18; col. 5, lines 6-15) or cysteamine (see claims 19-27; col. 5, lines 16-22) at predetermined intervals during the day. Unfortunately, some of the dosages of panthethine or cysteamine (for example, 500 mg of cysteamine) disclosed in the '519 patent are toxic to humans. In fact, such dosage amounts of cysteamine or panthethine can also cause undesirable gastrointestinal symptoms, such as increased acid output or even ulcers (Srivastava, P. K. & L. Field, J. Med. Chem., 18(8): 798-802, 1975). U.S. Pat. No. 6,686,337 discloses methods for treating Type II diabetes using a combination of a specified sulfamate and an antidiabetic agent.

SUMMARY OF THE INVENTION

An embodiment provides a method of treating a blood-glucose condition, comprising identifying a subject having a blood-glucose condition in need of treatment and administering to the subject an amount of a composition that is effective to modulate a blood-glucose level, wherein the composition comprises at least one selected from a non-sulfamate anticonvulsant; a psychotherapeutic agent; an opioid antagonist; a combination of a psychotherapeutic agent and an opioid antagonist; a combination of a psychotherapeutic agent and an anticonvulsant; a combination of an opioid antagonist and an anticonvulsant; and a combination of an opioid antagonist, an anticonvulsant, and a psychotherapeutic agent.

In some embodiments, the subject can suffer from at least one condition selected from diabetes, insulin resistance, hyperinsulinemia, impaired glucose metabolism, and hyperglycemia. In some embodiments, the condition is insulin resistance. In some embodiments, the condition is Type 2 diabetes.

Examples of suitable psychotherapeutic agents include: amitriptyline, aripiprazole, benzodiazepines, bupropion, carbamezepine, clomipramine, clozapine, desipramine, dothiapen, doxepin, elatriptan, other triptans, fluoxetine, imipramine, lamotrogine, lithium, maprotiline, mirtazapine, nortriptyline, olanzapine, oxycarbamezepine, paroxetine, protriptyline, quetiapine, risperidone, setiptiline, sumatriptan, tiagabine, trimipramine, valproate, ziprasidone, and zolmitriptan, or a pharmaceutically-acceptable salt or prodrug thereof. In some preferred embodiments, the psychotherapeutic agent is selected from: bupropion, mirtazapine, olanzapine, setiptiline, fluoxetine, and valproate, or a pharmaceutically-acceptable salt or prodrug thereof.

Examples of suitable anticonvulsants include: 5,5-diphenylhydantoin, benzodiazepine, carbamazepine, clonazepam, clorazepate, diazepam, divalproex, ethosuximide, felbamate, fosphenyloin, gabapentin, lamotrigine, levetiracetam, methsuximide, oxcarbazepine, phenyloin, pregabalin, tiagabine, topiramate, valproate, valproic acid, and zonisamide, or a pharmaceutically-acceptable salt or prodrug thereof. In some preferred embodiments, the anticonvulsant is zonisamide. The non-sulfamate anticonvulsant can be selected from zonisamide, valproate, and valproic acid, or a pharmaceutically-acceptable salt or prodrug thereof.

Examples of suitable opioid antagonists include: alvimopan, buprenorphine, lofexidine, nalmefene, nalorphine, naloxone, naltrexone, norbinaltorphimine, methylnaltrexone, pentacozine, and propiram, or a pharmaceutically-acceptable salt or prodrug thereof. In some preferred embodiments, the opioid antagonist is selected from: nalmefene, nalorphine, naloxone, naltrexone, and methylnaltrexone, or a pharmaceutically-acceptable salt or prodrug thereof.

In some embodiments, the composition that is effective to modulate a blood-glucose level can comprise a combination of a psychotherapeutic agent and an opioid antagonist. The psychotherapeutic agent can be selected from bupropion, mirtazapine, olanzapine, setiptiline, fluoxetine, and valproate, or a pharmaceutically-acceptable salt or prodrug thereof; and the opioid antagonist can be selected from nalmefene, nalorphine, naloxone, naltrexone, and methylnaltrexone, or a pharmaceutically-acceptable salt or prodrug thereof. In some embodiments, the psychotherapeutic agent can be administered to the subject separately from the opioid antagonist.

In some embodiments, the composition that is effective to modulate a blood-glucose level comprises a combination of a psychotherapeutic agent and an anticonvulsant. The psychotherapeutic agent can be selected from bupropion, mirtazapine, olanzapine, setiptiline, fluoxetine, and valproate, or a pharmaceutically-acceptable salt or prodrug thereof; and the anticonvulsant can be selected from topiramate, valproate, valproic acid, and zonisamide, or a pharmaceutically-acceptable salt or prodrug thereof. In some embodiments, the psychotherapeutic agent can be administered to the subject separately from the anticonvulsant.

In some embodiments, the composition that is effective to modulate a blood-glucose level comprises a combination of an opioid antagonist and an anticonvulsant. The opioid antagonist can be selected from: alvimopan, buprenorphine, lofexidine, nalmefene, nalorphine, naloxone, naltrexone, norbinaltorphimine, methylnaltrexone, pentacozine, and propiram, or a pharmaceutically-acceptable salt or prodrug thereof; and the anticonvulsant can be selected from topiramate, valproate, valproic acid, and zonisamide, or a pharmaceutically-acceptable salt or prodrug thereof. In some embodiments, the opioid antagonist is administered to the subject separately from the anticonvulsant.

In some embodiments, the composition that is effective to modulate a blood-glucose level comprises a combination of an opioid antagonist, an anticonvulsant, and a psychotherapeutic agent. The opioid antagonist can be selected from: alvimopan, buprenorphine, lofexidine, nalmefene, nalorphine, naloxone, naltrexone, norbinaltorphimine, methylnaltrexone, pentacozine, and propiram, or a pharmaceutically-acceptable salt or prodrug thereof; the anticonvulsant can be selected from topiramate, valproate, valproic acid, and zonisamide, or a pharmaceutically-acceptable salt or prodrug thereof; and the psychotherapeutic agent can be selected from bupropion, mirtazapine, olanzapine, setiptiline, fluoxetine, and valproate, or a pharmaceutically-acceptable salt or prodrug thereof. In some embodiments, at least one of the opioid antagonist, the anticonvulsant, and the psychotherapeutic agent can be administered to the subject separately from at least one of the others.

Any disclosed composition can further comprise insulin. Any disclosed composition can comprise a controlled release formulation, which can, in some embodiments, be a sustained release formulation.

In some embodiments, the disclosed methods comprise obtaining a measurement of the subject's blood glucose level. A dosage of the composition can be adjusted after obtaining the measurement of the subject's blood glucose level. The disclosed methods may comprise providing dietary instructions to the subject.

In some embodiments, the present invention relates to a package comprising a blood-glucose modulating composition in unit dosage form and written instructions advising the reader to monitor the blood-glucose level of an intended human recipient of the composition, wherein the blood glucose-modulating composition comprises at least one selected from: a non-sulfamate anticonvulsant; a psychotherapeutic agent; an opioid antagonist; a combination of a psychotherapeutic agent and an opioid antagonist; a combination of a psychotherapeutic agent and an anticonvulsant; a combination of an opioid antagonist and an anticonvulsant; and a combination of an opioid antagonist, an anticonvulsant, and a psychotherapeutic agent.

These and other embodiments are described in greater detail below.

DETAILED DESCRIPTION OF THE PREFERRED EMBODIMENT

It has been realized that melanocortin neurons influence insulin sensitivity (conversely, known as insulin insensitivity or insulin resistance). Embodiments of this invention include administering compositions that influence the activity of these neurons, thereby modulating blood-glucose levels and, e.g., altering, compensating for, or inhibiting the severity, risk, onset, and/or occurrence of blood-glucose conditions. In some embodiments, these blood-glucose modulating (BGM) compositions comprise at least one selected from a non-sulfamate anticonvulsant (e.g., zonisamide); a psychotherapeutic agent (e.g., an anti-depressant such as fluoxetine, bupropion, mirtazapine, olanzapine and/or paroxetine); an opioid antagonist e.g., naltrexone, nalmafene and.or naloxone); a combination of a psychotherapeutic agent and an opioid antagonist; a combination of a psychotherapeutic agent and an anticonvulsant; a combination of an opioid antagonist and an anticonvulsant; and a combination of an opioid antagonist, an anticonvulsant, and a psychotherapeutic agent. Examples of compounds that alter the activity of melanocortin neurons include compounds that increase agonism of a melanocortin 3 receptor (MC3-R) or a melanocortin 4 receptor (MC4-R) compared to normal physiological conditions. The compounds can include those that enhance α-MSH activity. These compounds can include psychotherapeutics. In some embodiments these also include anticonvulsants. Moreover, it has been realized that combinations of psychotherapeutics and anticonvulsants; psychotherapeutics and opioid antagonists; anticonvulsant and opioid antagonists; and/or psychotherapeutics, anticonvulsants, and opioid antagonists can have an even larger impact on melanocortin neurons and thus an even larger impact on insulin resistance. As such, by controlling the activity of melanocortin neurons, embodiments of this invention can provide a way to modulate blood glucose levels and thereby control, inhibit and/or prevent the onset, severity, risk, and/or occurrence of blood-glucose conditions. Similarly, various compositions comprising compounds that influence cells having melanocortin receptors are also provided.

In some aspects, a BGM composition having multiple compounds is provided. In some aspects, the BGM composition is used for treating insulin resistance and can comprise a first compound, which is an opioid antagonist, a second compound, which is a psychotherapeutic, and the third compound, which is an anticonvulsant, wherein each of the compounds is in present in sufficient amount to inhibit a blood-glucose condition. Any one, or combination of these compounds, can be administered to a person at risk of developing, or having, a blood-glucose condition and thereby decrease the patient's risk of developing a blood-glucose condition or inhibiting the severity, progression, and/or duration of a patient's blood-glucose condition.

In other aspects, the BGM composition comprises insulin or is further combined or administered with insulin, and thus can be used directly to treat and/or inhibit a blood-glucose condition, such as diabetes or insulin resistance, as well as reducing the risk and/or reversing any onset of a blood-glucose condition. Thus, in some embodiments, for example, the BGM composition comprises (1) an opioid antagonist and insulin, (2) a psychotherapeutic agent and insulin, (3) an anticonvulsant and insulin, (4) an opioid antagonist, insulin, and a psychotherapeutic agent, (5) an opioid antagonist, insulin, and an anticonvulsant, (6) insulin, a psychotherapeutic, and an anticonvulsant; or (7) insulin, a psychotherapeutic agent, an anticonvulsant, and an opioid antagonist. These BGM compositions can be effective for treating insulin resistance as well as other blood-glucose conditions, including Type 1 diabetes, Type 2 diabetes, diabetes associated with obesity or obsessive-compulsive disorder, "pre-diabetes" (e.g., pre-diabetic obesity) in which the blood glucose level is between about 110 and 125 mg/dl (fasting), drug-induced diabetes, gestational diabetes and diabetes associated with various medical disorders such as Cushing's syndrome. As will be appreciated by one of skill in the art, other BGM combinations are also contemplated. In some embodiments, a combination of insulin with a compound or method that alters the activity of melanocortin cells (e.g., neurons with melanocortin receptors) in a composition or method, is contemplated. These and other embodiments are discussed in greater detail below. The following definitions are provided to clarify some aspects of the relevant components and diseases.

Definitions

The term "blood-glucose condition" refers to a condition in which it is desirable to modulate a patient's glucose levels. In some embodiments, blood-glucose conditions include conditions in which it is desirable to reduce blood-glucose levels. For example, high blood-glucose levels can be a blood-glucose condition. In other embodiments, blood-glucose conditions include conditions in which it is desirable to maintain blood-glucose levels at a specific value or within a range of values. In still other embodiments, blood-glucose conditions include conditions in which it is desirable to increase blood-glucose levels. In some embodiments, methods and compositions described herein can be used to first reduce blood-glucose levels and to then maintain the blood-glucose levels at a specific value or within a range of values. Blood-glucose conditions include conditions in which a patient is at risk of developing a blood-glucose condition. In one embodiment, insulin resistance is a blood-glucose condition. In another embodiment, diabetes is a blood-glucose condition.

The term "insulin" refers to a polypeptide hormone (molecular weight of approximately 5700) naturally produced by the pancreas (secreted by beta cells in the islets of Langerhans) of a mammal which controls the amounts of glucose present in the blood by stimulating the uptake of glucose by muscle and adipose tissue. Insulin can exist in various states, such as preproinsulin and proinsulin. The term "insulin" also refers to synthetic versions, such as Humulin® (available commercially from Eli Lilly).

The term "insulin sensitivity" refers to the capacity of a cell, for example, a muscle cell (e.g., skeletal muscle cell) or fat cell (e.g., an adipocyte), or organism to sense or respond to stimulation by insulin or to insulin signaling. The preferred response to insulin or insulin signaling is glucose uptake.

The term "insulin resistance" refers to a condition or disorder in which the tissues of the body fail to respond normally to insulin. Insulin resistance manifests itself in pathologically elevated endogenous insulin and glucose levels and predisposes a mammal to the development of a cluster of abnormalities, including some degree of impaired glucose tolerance, an increase in plasma triglycerides and low density lipoprotein cholesterol (LDL) levels, a decrease in high-density lipoprotein cholesterol (HDL) levels, high blood pressure, hyperuricemia, a decrease in plasma fibrinolytic activity, an increase in cardiovascular disease and atherosclerosis (Reaven, G. M. *Physiol Rev.* 75(3): 473-86, 1995). Decompensated insulin resistance is widely believed to be an underlying cause of non-insulin dependent diabetes mellitus (NIDDM). Hyperinsulinemia refers to the overproduction of insulin by pancreatic cells. Often, hyperinsulinemia occurs as a result of insulin resistance, which is a condition defined by cellular resistance to the action of insulin. Insulin resistance, as defined above, is a state/disorder in which a normal amount of insulin produces a subnormal biologic (metabolic) response. In insulin-treated patients with diabetes, insulin resistance is considered to be present whenever the therapeutic dose of insulin exceeds the secretory rate of insulin in normal person.

Impaired glucose homeostasis (or metabolism) refers to a condition in which blood sugar levels are higher than normal but not high enough to be classified as diabetes. There are two categories that are considered risk factors for future diabetes and cardiovascular disease. Impaired glucose tolerance (IGT) occurs when the glucose levels following a 2-hour oral glucose tolerance test are between 140 and 199 mg/dl. IGT is a major risk factor for Type 2 diabetes and is present in about 11% of adults, or approximately 20 million Americans. About 40-45% of persons age 65 years or older have either Type 2 diabetes or IGT. Impaired fasting glucose (IFG) occurs when the glucose levels following an 8-hour fasting plasma glucose test are between 110 and 126 mg/dl.

Hyperglycemia, a common feature of diabetes, is caused by decreased glucose utilization by liver and peripheral tissues and an increased glucose production by liver.

The term "compound" can refer to many different substances. For example, the first compound generally denotes an opioid antagonist, the second compound generally denotes an α-MSH activity enhancer or psychotherapeutic, and the third compound generally denotes an anticonvulsant. However, where explicitly denoted, these terms can take on different meanings. Generally, "compound" does not encompass insulin, unless explicitly denoted.

The term "pharmaceutically-acceptable salt" refers to a formulation of a compound that does not cause significant irritation to an organism to which it is administered and does not abrogate the biological activity and properties of the compound. Pharmaceutically-acceptable salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically-acceptable salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, and salts thereof with amino acids such as arginine, lysine, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial. A further example of a prodrug might be a short peptide (polyaminoacid) bonded to an acid group where the peptide is metabolized to provide the active moiety.

The term "pharmaceutical composition" refers to a mixture of an active compound (or combination of active compounds) with other chemical components, such as diluents or carriers. The pharmaceutical composition facilitates administration of the active compound to an organism. Multiple techniques of administering a compound exist in the art including, but not limited to, oral, injection, aerosol, parenteral, and topical administration, and a variety of chemical components have been developed for admixture with the active compound(s) to facilitate such administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in solutions, such as water, that will dissolve the compound of interest as well as stabilize the biologically active form of the compound. Salts dissolved in buffered solutions are utilized as diluents in the art. One commonly used buffered solution is phosphate buffered saline (PBS) because it mimics the salt conditions of human blood. Since buffer salts can control the pH of a solution at low concentrations, a buffered diluent rarely modifies the biological activity of a compound.

The term "treatment" does not necessarily mean curing a disease or disorder. A reduction in symptoms associated with the disorder or disease can also be characterized as a treatment. Further, a slowing in the progression of the disorder or disease can also be characterized as a treatment.

The term "insulin sensitizing" denotes that the compound makes a host or subject more sensitive to the presence of insulin, whether it be exogenous or endogenous insulin.

The term "physiologically acceptable" characterizes a carrier or diluent that does not abrogate the biological activity and properties of the compound.

The term "effective amount" denotes the amount of a substance required to achieve the particular utility. Thus, an effective amount can vary depending upon a particular use.

The term "inhibit" characterizes a decrease in the risk, time of onset, side effects, symptoms, and/or progression of a condition during a specified treatment compared to the risk, time of onset, side effects, symptoms, and/or progression of the condition predicted without the specified treatment. Comparisons can also be performed between two treatment options. For example, an opioid antagonist would be said to inhibit a condition if the risk, time of onset, side effects, symptoms and/or progression of the condition were decreased when a patient was administered both an opioid antagonist and insulin compared to administration of insulin. In some embodiments, a condition is inhibited if the condition is completely reversed or prevented from occurring. The severity of a symptom can be measured as a deviation in the host of some quantifiable amount from the norm (e.g., blood sugar or insulin levels), or, for example, as an amount of a medication that is given to the host (e.g., the host requires 30% less externally administered insulin for the desired effect when the host is also administered an anticonvulsant).

Throughout the present disclosure, when a particular compound is mentioned by name, for example, zonisamide, bupropion, naltrexone, fluoxetine, setiptiline, mirtazapine, or valproate, it is understood that the scope of the present disclosure encompasses active metabolites, pharmaceutically-acceptable salts, esters, amides, and/or prodrugs of the named compound. Also, if the named compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the named compound comprises more than one chiral center, the scope of the present disclosure also includes compositions comprising a mixture of the various diastereomers, as well as compositions comprising each diastereomer substantially free of the other diastereomers. Thus, for example, commercially available mirtazapine is a racemic mixture comprising two separate enantiomers. The recitation of "mirtazapine" throughout this disclosure includes compositions that comprise the racemic mixture of mirtazapine, the compositions that comprise the (+) enantiomer substantially free of the (−) enantiomer, and the compositions that comprise the (−) enantiomer substantially free of the (+) enantiomer.

In addition, active metabolites of the various compounds described herein are also within the scope of the present invention. For example, the 6-β-hydroxynaltrexone metabolite of naltrexone is active, as is the norfluoxetine metabolite of fluoxetine. Fluoxetine is converted into both S-norfluoxetine (80% of total) and R-norfluoxetine (20% of total). Both of these metabolites are active and are contemplated for use in the compositions and methods described herein.

Compounds

As discussed above, in one aspect, a BGM composition for the treatment or inhibition of blood-glucose conditions is provided. In general, these BGM compositions comprise one or more active compounds selected from the group consisting of an opioid antagonist (e.g., naltrexone), an MC3-R/MC3-R agonist or α-MSH activity enhancer (e.g., psychotherapeutic agent), and an anticonvulsant (e.g., zonisamide). Non-sulfamate anticonvulsants are preferably included in BGM compositions that do not contain BGM amounts of an opioid antagonist or MC3-R/MC3-R agonist or α-MSH activity enhancer. Likewise, when an anticonvulsant in not administered in combination with BGM amounts of an opioid antagonist or MC3-R/MC3-R agonist or α-MSH activity enhancer, the anticonvulsant is preferably a non-sulfamate anticonvulsant. These BGM compositions can be used in amounts effective for the inhibition of insulin resistance. Additionally, they can also be used to inhibit or treat Type 1 or Type 2 diabetes, or any disorder of glucose dysregulation, including those mentioned above. In some embodiments, the BGM composition further comprises insulin, which can be used to treat a blood-glucose condition, such as Type 1 diabetes, while reducing the risk that insulin resistance will occur. Additionally, this combination of the BGM composition and insulin can be used to treat a blood-glucose condition, such as Type 2 diabetes, by allowing additional exogenous insulin to be administered to the subject while the insulin resistance aspect of the disorder is addressed by one or more of the above compounds. The BGM composition can comprise any one of the compounds or any combination of the compounds and the insulin in an effective amount. In some embodiments, the amount of each compound and insulin used is at least an effective amount and is preferably less than an amount that results in significant, unwanted side effects. In some embodiments, the amount is about a minimal amount that is at least an effective amount.

In some embodiments the psychotherapeutic agent, or α-MSH activity enhancer, is an antidepressant, an antimigrane, an antibipolar, an antimania drug, a mood stabilizer, or an antiepileptic. Examples of antidepressants include bupropion, paroxetine, fluoxetine and mirtazapine. Examples of antimigrane drugs include sumatriptan, zolmitriptan, elatriptan and other triptans. Examples of antibipolar drugs include lithium, valproate, carbamezepine, oxycarbamezepine, lamotrogine, tiagabine, olanzapine, clozapine, risperidone, quetiapine, aripiprazole, ziprasidone, and benzodiazepines. In some embodiments, the psychotherapeutic comprises a salt of lithium. In other embodiments, the psychotherapeutic is valproate, which includes both the salt of valproate and the free acid form of valproic acid. Also included are pharmaceutically acceptable salts or prodrugs of these drugs, controlled release (e.g., sustained or extended release) formulations of the above drugs, as well as combinations of the above drugs. In some embodiments, the lithium salt may be lithium carbonate or lithium citrate. In some embodiments, the lithium drug is in an extended release formulation. In other embodiments, more than one psychotherapeutic agent is included in the BGM composition and/or method.

In some embodiments, the present invention is directed to BGM compositions comprising insulin, zonisamide, and a salt of lithium, as described herein and in formulations described herein. In other embodiments, the present invention is directed to compositions comprising insulin, zonisamide, and valproic acid, and/or a pharmaceutically-acceptable salt, such as different salts of valproate, ester, amide, or prodrugs thereof.

Zonisamide is a marketed anticonvulsant indicated as adjunctive therapy for adults with partial onset seizures. Without being bound by any particular theory, it is believed that the mechanism of antiepileptic activity appears to be: 1) sodium-channel blocking; and, 2) reduction of inward T-type calcium currents. In addition, zonisamide binds to the GABA/benzodiazepine receptor complex without producing change in chloride flux. Further, zonisamide facilitates serotonergic and dopaminergic neurotransmission and possesses a weak inhibitory effect on carbonic anhydrase.

In certain embodiments, the antidepressant is mirtazapine or an analogous compound of Formula I (I)

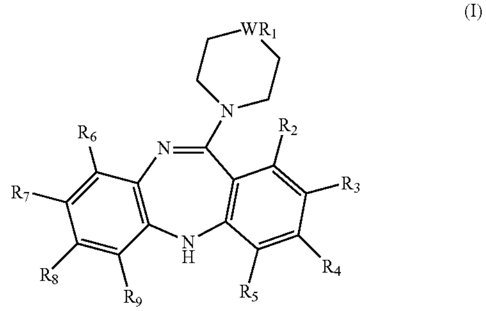

where

W is nitrogen, CH, oxygen, or sulfur;

$R_1$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, optionally substituted $C_{1-6}$ alkoxyalkyl, and optionally substituted aryl and arylalkyl;

$R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, heteroalkyl, and $NO_2$;

$R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, heteroalkyl, and $NO_2$; and $R_{10}$ is $C_{1-6}$ alkyl.

The administration of both an opioid antagonist and a psychotherapeutic agent can have a synergistic effect on modulating blood glucose and/or inhibiting insulin resistance compared to the effect of the compounds alone. The administration of both an opioid antagonist and an anticonvulsant can have a synergistic effect on modulating blood glucose and/or inhibiting insulin resistance compared to the effect of the compounds alone. The administration of both an anticonvulsant and a psychotherapeutic agent can have a synergistic effect on modulating blood glucose and/or inhibiting insulin resistance compared to the effect of the compounds alone. Further, the administration of an anti-diabetic medication and an opioid antagonist, a psychotherapeutic agent, an anticonvulsant or a combination thereof can also have a synergistic effect on modulating blood glucose and/or inhibiting insulin resistance. Examples of opioid antagonists include alvimopan, norbinaltorphimine, nalmefene, naloxone, naltrexone, methylnaltrexone, and nalorphine, and pharmaceutically-acceptable salts or prodrugs thereof.

As will be appreciated by one of skill in the art, there are a variety of ways in which the compounds above can be administered and the timing involved in the administration. Some of these are discussed below; others will be appreciated from the present description by one of skill in the art.

In another embodiment, the antidepressant to be administered either by itself or with or combined with other compounds and/or insulin is a tricyclic antidepressant. Examples of tricyclic antidepressants include, but are not limited to, imipramine, desipramine, trimipramine, nortriptyline, clomipramine, doxepin, amitriptyline, protriptyline, dothiapen, and maprotiline. Maprotiline, a very effective antidepressant, is not used widely because it carries risk of seizures. The combination of maprotiline and zonisamide or other anticonvulsants has the added benefit of reducing the risk of seizures, in addition to reducing the risk of weight gain due to the use of the antidepressant. Non-limiting examples of useful antidepressants include fluoxetine, bupropion, mirtazapine, olanzapine and/or paroxetine, In further embodiments, the antidepressant to be administered either by itself or with or combined with other compounds and/or insulin is a monoamine oxidase inhibitor (MAO inhibitor). Examples of MAO inhibitors include, but are not limited to, phenelzine (Nardil®), tranylcypromine (Parnate®), isocarboxazid (Marplan®) and moclobemide (Aurorix®).

In certain embodiments, the antihistamine to be administered either by itself or with or combined with other compounds and/or insulin is one of setiptilinie, teciptiline, ORG 8282 (Organon, Netherlands), or MO 8282 (Mochida, Japan).

In some embodiments, the $5HT_{2C}$ receptor antagonist to be administered either by itself or with or combined with other compounds and/or insulin is selected from colozapine, N-desmethylclozapine, and clozapine-N-oxide.

In some embodiments, the first or second compound is an anticonvulsant, which is to be administered either by itself or with or combined with other compounds and/or insulin. Examples of anticonvulsants include barbiturates, benzodiazepines, GABA analogues, hydantoins, miscellaneous anticonvulsants, phenyltriazines, and succinimides. An example of a barbiturate includes pentobarbital. Examples of benzodiazepines include clonazepam, clorazepate, benzodiazepine, and diazepam. Examples of GABA analogues include tiagabine, pregabalin, and gabapentin. Examples of hydantoins include fosphenyloin, phenyloin, and 5,5-Diphenylhydantoin. Examples of miscellaneous anticonvulsants include carbamazepine, valproate, valproic acid, divalproex, felbamate, levetiracetam, carbamazepine, topiramate, oxcarbazepine, and zonisamide. An example of a phenyltriazine is lamotrigine. Examples of succinimides include methsuximide and ethosuximide. Also included are extended release formulations of the above drugs, pharmaceutically-acceptable salts or prodrugs thereof, as well as combinations of the above drugs.

In one embodiment, the present invention is directed to a BGM composition for the treatment of insulin resistance comprising zonisamide and mirtazapine. In another embodiment, the present invention is directed to a BGM composition for the treatment of insulin resistance comprising zonisamide and paroxetine. In yet another embodiment, the present invention is directed to a BGM composition for the treatment of insulin resistance comprising zonisamide and venlafaxine. In some embodiments, the above embodiments are further combined with insulin, allowing for the treatment or inhibition of a blood-glucose condition upon the administration of the insulin.

In some embodiments, the present invention is directed to a BGM composition for inhibiting a blood-glucose condition, comprising bupropion and mirtazapine. In further embodiments, the present invention is directed to a BGM composition for inhibiting a blood-glucose condition, comprising zonisamide and setiptiline. In other embodiments, the present invention is directed to a BGM composition for inhibiting a blood-glucose condition comprising, bupropion and setiptiline. In other embodiments, the present invention is directed to a BGM composition for inhibiting a blood-glucose condition, comprising bupropion and naltrexone. In yet other embodiments, the present invention is directed to a BGM composition for inhibiting a blood-glucose condition, comprising fluoxetine and naltrexone. In other embodiments, the present invention is directed to a BGM composition for inhibiting a blood-glucose condition, comprising zonisamide, bupropion, and mirtazapine. In yet other embodiments, the present invention is directed to a BGM composition for inhibiting a blood-glucose condition, comprising zonisamide, bupropion, and setiptiline. In some embodiments, in each of the above embodiments, insulin is also included.

As will be appreciated by one of skill in the art, when insulin is included with the above compounds, the amount of insulin used may be an amount that is effective for the treatment of a subject's diabetes in the presence of the above compounds. Thus, basal insulin levels are contemplated as well as bolus levels (e.g., for meals). The administration of insulin with the above compounds allows for lower levels of insulin to be more effective in resulting in a desired goal (e.g., a particular insulin or blood sugar level). Thus, the use of lower levels of insulin will help to inhibit the onset of a blood-glucose condition. In some embodiments, the amount of insulin administered, when administered with one or more of the compounds described herein is less than would otherwise be administered to achieve the same blood sugar level in the subject. For example, the amount of insulin can be reduced by 1-10, 10-20, 20-30, 30-40, 450-50, 50-60, 60-70, 70-80, 80-90, 90-99% or more when the above compounds are used.

Insulin can be part of the composition(s) by which the compounds are administered. Thus, in some embodiments, insulin is contained in the pharmaceutical preparation with the above compounds. In other embodiments, the insulin is separate from the above compounds. In other embodiments, a subject no longer needs to take exogenous insulin, as the patient is only suffering from insulin resistance, which was reduced or reversed by the above compounds, allowing the normal doses of endogenous insulin to be sufficient for the subject.

Method of Treatment

In another aspect, the present invention relates to a method of inhibiting a blood-glucose condition comprising identifying an individual in need thereof and treating that individual with an amount of a BGM composition as described herein that is effective to modulate a blood glucose level. In an embodiment, the BGM composition comprises a psychotherapeutic agent (e.g. an α-MSH activity enhancer) and an anticonvulsant. The psychotherapeutic agent and the anticonvulsant are as described above. In some embodiments, the above BGM compositions and the following methods are used to inhibit Type 2 diabetes. In other embodiments, they are used to inhibit Type 1 diabetes. In some embodiments, these are administered with insulin, allowing for less insulin to be administered to a subject. In some embodiments, the method involves identifying a subject in need of treatment or preventative measures and then administering the above compounds or BGM compositions to the subject. Optionally, exogenous insulin can also be administered to the subject. Preferably, the amount of the compounds or insulin is low enough to minimize side effects, but high enough to be effective for inhibiting a blood-glucose condition. In one embodiment, the blood-glucose condition is caused by administration of a psychotherapeutic agent and/or anticonvulsant.

In another aspect, the present invention relates to inhibiting a blood-glucose condition comprising identifying an individual in need thereof and treating that individual with a BGM composition as described herein. In an embodiment, the BGM composition comprises a first compound that antagonizes opioid receptor activity and a second compound that enhances α-MSH activity. In some embodiments, opioid receptor activity is antagonized by administering an opioid receptor antagonist. The opioid receptor antagonist may be a μ-opioid receptor (MOP-R) antagonist. In some embodiments, the opioid receptor antagonist is selected from alvimopan, norbinaltorphimine, nalmefene, naloxone, naltrexone, methylnaltrexone, and nalorphine, and pharmaceutically-acceptable salts or prodrugs thereof.

In some of the embodiments set forth above, α-MSH activity is enhanced by administering a psychotherapeutic compound, e.g., as the second compound in the combinations described herein, where the psychotherapeutic compound triggers release of α-MSH or increases the activity of neurons that express α-MSH. In some embodiments, the psychotherapeutic compound is a selective serotonin reuptake inhibitor (SSRI) or a specific 5-HT receptor agonist (e.g. 2C agonist, 1B agonist, 5HT1*b* agonist or 5HT2*c* agonist). Although these specific receptors are more commonly found in rodents, it is understood by those of skill in the art that other mammals have serotonin receptors on various neurons that are analogous in function and form to these receptors. Agonists (or antagonists) of these non-rodent, preferably human, serotonin receptors are within the scope of the present invention. Examples of SSRIs that can be used in the present invention include fluoxetine, fluvoxamine, sertraline, paroxetine, citalopram, escitalopram, sibutramine, duloxetine, and venlafaxine, and pharmaceutically-acceptable salts or prodrugs thereof.

In other embodiments, the second compound is a γ-amino butyric acid (GABA) inhibitor, a GABA receptor antagonist or a GABA channel antagonist. By "GABA inhibitor" it is meant a compound that reduces the production of GABA in the cells, reduces the release of GABA from the cells, or reduces the activity of GABA on its receptors, either by preventing the binding of GABA to GABA receptors or by minimizing the effect of such binding. The GABA inhibitor may be a 5-HT1*b* receptor agonist. The GABA inhibitor may suppress the expression of the agouti-related peptide (AgRP) gene, or it may suppress the production or release of AgRP. The GABA inhibitor may suppress the suppression or release of neuropeptide Y (NPY). In certain embodiments, the GABA inhibitor suppresses the activity of neurons that express AgRP. For example, the GABA inhibitor may be topiramate, 1-(2-(((diphenylmethylene)amino)oxy)ethyl)-1,2,5,6-tetrahydro-3-pyridinecarboxylic acid hydrochloride (NNC-711), or vigabatrin. It is, however, understood that a 5-HT1b agonist may inhibit the NPY/AgRP/GABA neuron (and therefore activate POMC neurons) without acting as an inhibitor of the GABA pathway.

In certain other embodiments, the GABA inhibitor increases the expression of proopiomelanocortin (POMC) neurons, leading to greater agonism at MC3-R and/or MC4-R. In some of these embodiments, the GABA inhibitor increases the production or release of POMC protein. In certain other of these embodiments, the GABA inhibitor increases the activity on POMC expressing neurons. In some embodiments, the GABA inhibitor is topiramate.

In other embodiments, the second compound is a dopamine reuptake inhibitor. Phentermine is an example of a dopamine reuptake inhibitor. In certain other embodiments, the second compound is a norepinephrine reuptake inhibitor. Examples of norepinephrine reuptake inhibitors include bupropion, thionisoxetine and reboxetine. Other embodiments include those in which the second compound is a dopamine agonist. Dopamine agonists include cabergoline, amantadine, lisuride, pergolide, ropinirole, pramipexole and bromocriptine. In further embodiments, the second compound is a norepinephrine releaser, for example diethylpropion, or a mixed dopamine/norepinephrine reuptake inhibitor, for example, atomoxatine.

In certain other embodiments, the second compound is a 5-HT1*b* agonist, such as sumatriptan, almotriptan, naratriptan, frovatriptan, rizatriptan, zomitriptan and/or elitriptan.

In another aspect, the present invention relates to inhibiting a blood-glucose condition comprising identifying an individual in need thereof and treating that individual with a an effective amount of a BGM composition comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions.

In certain embodiments, the opioid antagonist antagonizes a MOP-R in a mammal. The mammal may be selected from the group consisting of mice; rats; rabbits; guinea pigs; dogs; cats; sheep; goats; cows; primates, such as monkeys, chimpanzees and apes; and humans.

In some embodiments, the opioid antagonist is selected from alvimopan, norbinaltorphimine, nalmefene, naloxone, naltrexone, methylnaltrexone, and nalorphine, and pharmaceutically-acceptable salts or prodrugs thereof. In other embodiments, the opioid antagonist is a partial opioid agonist. Compounds of this class have some agonist activity at opioid receptors. Examples of partial opioid agonists include pentacozine, buprenorphine, nalorphine, propiram and lofexidine.

In some embodiments, a subject or patient to receive the treatment is identified by identifying a patient with diabetes; this can be Type 1 and/or Type 2 diabetes. In some embodiments, the patient or subject is identified by identifying a patient with insulin resistance. In some embodiments, the patient or subject is identified by identifying a patient with insulin resistance. In other embodiments, the patient or subject is identified by identifying a patient with hyperinsulinemia. In other embodiments, the patient or subject is identified by identifying a patient with impaired glucose metabolism (impaired glucose tolerance or impaired fasting glucose). In other embodiments, the patient or subject is identified by identifying a patient with hyperglycemia. This can be done by measuring the absolute or relative amount of insulin given to the patient and the resulting change in blood sugar therefrom, or by simply determining the amount of insulin given to a patient and if that amount is greater than the expected endogenous amount. Alternatively, this can be done by noting an increase in the amount of insulin required for a patient to get a particular goal or result. In some embodiments, any patient or subject taking insulin can benefit from the above compositions or methods. In other embodiments, any of the above compounds (e.g., opioid antagonist, psychotherapeutic, anticonvulsant, or combinations thereof) can be used alone to one or more of the above conditions, simply by administering the compound(s) to the subject and allowing the subject's endogenous insulin levels to control the subject's blood sugar levels.

In further embodiments of this invention, a patient is already being administered composition comprising a psychotherapeutic agent (e.g., an antipsychotic), an opioid antagonist, an anticonvulsant, or some combination thereof for a non-glucose-related purpose and is in need of treatment of a blood-glucose condition. In these embodiments the quantity of the composition being administered can be modulated in order to inhibit the blood-glucose condition. In some of these embodiments, the blood-glucose condition is one in which it is desirable to increase blood glucose levels. In some of these embodiments, the amount of the composition being administered can be reduced.

In some embodiments, inhibiting a blood-glucose condition comprises administering to the individual an effective amount of a BGM composition comprising a psychotherapeutic agent (an α-MSH activity enhancer) and an anticonvulsant. In some embodiments the psychotherapeutic agent and the anticonvulsant are administered more or less simultaneously. In other embodiments the psychotherapeutic agent is administered prior to the anticonvulsant. In yet other embodiments, the psychotherapeutic agent is administered subsequent to the anticonvulsant. These compounds can be administered substantially simultaneously with insulin, thereby making insulin more effective in lowering blood sugar levels. Alternatively, insulin can be administered with one compound and the other compound added later. Alternatively, insulin can be administered before the compounds. As will be appreciated by one of skill in the art, the speed with which the above compounds act and the duration for which they act can determine when, how, and how much insulin should be added. Of course, these orders and methods can apply to any of the compounds, including the opioid antagonist.

In certain embodiments, the compounds of the BGM composition are administered individually or separately; in other embodiments they are administered together. In other embodiments, the compounds are covalently linked to each other such that they form a single chemical entity. The single chemical entity is then digested and is metabolized into two separate physiologically active chemical entities; one of which is one compound (e.g., a psychotherapeutic) and the other one is the other compound (e.g., anticonvulsant). The linked compound can be mixed with insulin for administration. In some embodiments, insulin is also linked to one or both of the compounds. The chemical linkage is selected such that after entry into the body, the linkage is broken, such as by enzymatic action, acid hydrolysis, base hydrolysis, or the like, and the two separate compounds are then formed.

Aspects of the present invention provide, at least in part, for methods of inhibiting the risk, side effects, or symptoms of a blood-glucose condition, such as insulin resistance or type 2 diabetes. These methods can involve the use of BGM compositions comprising anticonvulsants and/or any of the compounds disclosed herein. In some embodiments, insulin resistance is completely reversed or prevented from occurring. In other embodiments, the symptoms are only lessened or delayed from symptoms predicted without administration of the composition. In some embodiments, the addition of one of the above compounds to insulin (e.g., an anticonvulsant, a psychotherapeutic, and/or an opioid antagonist) can be used to reduce a symptom(s) by 1-10, 10-20, 20-30, 30-40, 40-50, 50-60, 60-70, 70-80, 80-90, 90-99, or 100%. Symptoms or the severity of a symptom can be measured as a deviation in the host of some quantifiable amount from the norm (e.g., blood sugar or insulin levels), or, for example, as an amount of a medication that is given to the host (e.g., the host requires 30% less externally administered insulin for the desired effect when the host is also administered an anticonvulsant).

In certain embodiments, the anticonvulsant is effective in reducing convulsions associated with a blood-glucose condition in a mammal. The mammal may be selected from the group consisting of mice; rats; rabbits; guinea pigs; dogs; cats; sheep; goats; cows; primates, such as monkeys, chimpanzees, and apes; and humans. As will be appreciated by one of skill in the art, the anticonvulsant need not actually prevent a convulsion in a subject that is not suffering from a risk or likelihood of a convulsion. When the phrase "reducing convulsions" is used, it denotes the fact that, if the particular treatment had been administered to a patient suffering from a risk of a convulsion, that, the patient's risk of a convulsion would have decreased. However, a risk of convulsion actually need not occur in a patient who is not at risk of suffering from a convulsion. Rather, what is denoted is that similar biochemical mechanisms or pathways are being activated or suppressed in both patients.

In certain embodiments, the first compound of the BGM composition is zonisamide and the second compound is mirtazapine. In other embodiments, the first compound is bupropion and the second compound is mirtazapine. In further embodiments, the first compound is zonisamide and the second compound is setiptiline. In other embodiments, the first compound is bupropion and the second compound is setiptiline. In additional embodiments, the first compound is a combination of zonisamide and bupropion and the second compound is mirtazapine. In yet other embodiments, the first compound is a combination of zonisamide and bupropion and the second compound is setiptiline. As will be appreciated by one of skill in the art, any of the above compounds can be mixed with insulin or administered with insulin.

In some embodiments, the first compound is zonisamide and the second compound is a salt of lithium, as described herein and in formulations described herein. In other embodiments, the first compound is zonisamide and the second compound is valproic acid, or a pharmaceutically-acceptable salt, such as different salts of valproate, ester, amide, or prodrugs thereof. As will be appreciated by one of skill in the art, any of the above compounds can be mixed with insulin or administered with insulin.

In some embodiments, the first compound of the BGM composition is topiramate and the second compound is a salt of lithium, as described herein and in formulations described herein. In other embodiments, the first compound is topiramate and the second compound is valproic acid, or a pharmaceutically-acceptable salt, such as different salts of valproate, ester, amide, or prodrugs thereof. As will be appreciated by one of skill in the art, any of the above compounds can be mixed with insulin or administered with insulin.

In one embodiment, the methods comprise administering to a mammal receiving insulin an amount of zonisamide, at least sufficient to inhibit the risk of a subject experiencing a blood-glucose condition. In an alternative embodiment, the methods comprise administering to mammal receiving an antidepressant; a combination of zonisamide or topiramate, or other anticonvulsant (including agents that block kainate/AMPA (D,L-α-amino-3-hydroxy-5-methyl-isoxazole propionic acid) subtype glutamate receptors); and bupropion, or other compound that enhances the activity of norepinephrine and/or dopamine via uptake inhibition or other mechanism, in an amount sufficient to reduce the risk that a subject will experience a blood-glucose condition.

In certain embodiments, the insulin sensitizing agents for use in the methods of the present invention include zonisamide or topiramate (and pharmaceutically-acceptable salts thereof). In other embodiments, other methane-sulfonamide derivatives, such as those described in U.S. Pat. No. 4,172,896, or other sulfamates (including sulfamate-substituted monosaccharides), such as those described in U.S. Pat. No. 4,513,006 are used. Both of these references are incorporated by reference herein in its entirety. In other embodiments, particularly those involving the use of an anticonvulsant without a psychotherapeutic agent or an opioid agonist, the anticonvulsant is a non-sulfamate anticonvulsant. Zonisamide is an example of a non-sulfamate anticonvulsant.

In further embodiments, the insulin sensitizing agent is bupropion; while in other embodiments, one or more compounds disclosed in U.S. Pat. Nos. 3,819,706 and 3,885,046, both of which are incorporated by reference herein in their entirety, is used. In additional embodiments, the insulin sensitizing agent is a compound that enhances the activity of norepinephrine and/or dopamine, such as by reuptake inhibition or other mechanism. An insulin sensitizing agent is one that reduces the likelihood that a blood-glucose condition will occur in a patient and can include, for example, opioid antagonists, psychotherapeutic, and anticonvulsants.

Compounds that enhance the activity of norepinephrine and/or dopamine include norepinephrine agonists, such as phendimetrazine and benzphetamine; norepinephrine reuptake inhibitors such as atomoxetine, bupropion, thionisoxetine, and reboxetine; dopamine agonists, such as cabergoline, amantadine, lisuride, pergolide, ropinirole, pramipexole, and/or bromocriptine; norepinephrine releasers, for example diethylpropion; a mixed dopamine/norepinephrine reuptake inhibitor, for example, bupropion; a combination of a dopamine reuptake inhibitor and a norepinephrine reuptake inhibitor, e.g. bupropion and mazindol; or a combination of a selective serotonin reuptake inhibitor (SSRI) and a norepinephrine reuptake inhibitor, such as sibutramine, venlafaxine, and duloxetine.

Patients and subjects suitable for treatment include those identified as such, as described above, as well as those receiving insulin, an insulin derivative, or a compound that modulates blood sugar levels in a subject or patient.

In accordance with the invention, the combination of, for example, zonisamide or topiramate with bupropion (including controlled release forms such as sustained release preparations) provides an effective means of inhibiting a blood-glucose condition. The combination can be more effective than, for example, zonisamide or topiramate treatment alone and with fewer side effects. Neuropharmacologically, all three major nerve transmitters, e.g., serotonin, norepinephrine and dopamine, are targeted with the combination of, for example, bupropion with either zonisamide or topiramate. Side effects of, for example, zonisamide or topiramate (such as somnolence, psychomotor slowing, cognitive impairment, fatigue and depression) can be offset by insomnia, activation, psychomotor agitation and antidepressant effects of, for example, bupropion. On the other hand, zonisamide or topiramate, for example, can reduce the seizure risk associated with, for example, bupropion. Lower doses of both types of medication can be used in the combination treatment, thereby further reducing the overall side effect burden. Of course, insulin can be added to any of the above combinations in order to provide a convenient and reliable means for administering the desired compounds to a subject with the insulin the subject is to receive.

With regard to the pharmacokinetics of zonisamide, its renal excretion and minimal potential for inhibition or induction of hepatic microsomal enzymes, are favorable qualities in the concept of combination use with antidepressants, particularly newer generation antidepressants. The following section describes various pharmaceutical compositions which can be further embodiments of the compositions described above and used in the methods described above as well.

Pharmaceutical Compositions

In another aspect, the invention relates to a pharmaceutical composition comprising a combination of a psychotherapeutic agent, an anticonvulsant, and/or insulin, as described above, or comprising a linked molecule, as described herein, and a physiologically-acceptable carrier, diluent, or excipient, or a combination thereof.

Details of some embodiments of the appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein, all of which are incorporated by reference herein in their entirety, including any drawing. As will be appreciated by one of skill in the art, any method that is appropriate for delivery of insulin or for at least one of the compounds can be appropriate for delivery of the combination. For example, the compounds can be administered subcutaneously, all in one injection.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990. The following discussion, regarding pharmaceutical compositions and methods of administration, can apply not only to the compounds, but the compositions as a whole and any insulin as well.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. In some embodiments, at least one component of the composition can be administered by one administration route while at least one other component of the composition can be administered by another administration route. For example, insulin can be administered by subcutaneous injections and an antipsychotic can be administered orally.

Alternatively, one may administer the compound and/or insulin in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the compounds of the invention and/or insulin may be formulated in aqueous solutions, preferably in physiologically-compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds and/or insulin can be formulated readily by combining the active compounds with pharmaceutically-acceptable carriers well known in the art. Such carriers enable the compounds and/or insulin of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipients with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Controlled release forms of the BGM compositions described herein are specifically contemplated, including sustained release formulations. Methods for formulating controlled release forms are known to those skilled in the art and may be applied to make controlled release BGM compositions using routine experimentation informed by the guidance provided herein.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally, including sublingually, which include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds and/or insulin may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the BGM compositions may take the form of tablets or lozenges formulated in conventional manner.

For administration by inhalation, the compounds and/or insulin for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The BGM compositions and/or insulin may be formulated for parenteral administration by injection, e.g., by bolus injection or continuous infusion. Formulations for injection may be presented in unit dosage form, e.g., in ampoules or in multi-dose containers, with an added preservative. The BGM compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds and/or insulin may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and/or insulin to allow for the preparation of highly concentrated solutions.

Alternatively, the active ingredient may be in powder form for constitution with a suitable vehicle, e.g., sterile pyrogen-free water, before use.

The compounds and/or insulin may also be formulated in rectal compositions such as suppositories or retention enemas, e.g., containing conventional suppository bases such as cocoa butter or other glycerides.

In addition to the formulations described previously, the compounds and/or insulin may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds and/or insulin of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds and/or insulin may be employed. Liposomes and emulsions are well known examples of delivery vehicles or carriers for hydrophobic drugs. Certain organic solvents, such as dimethylsulfoxide, also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds and/or insulin used in the pharmaceutical compositions of the invention may be provided as salts with pharmaceutically-compatible counterions. Pharmaceutically-compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical BGM positions suitable for use in the present invention include compositions where the active ingredients are contained in an amount effective to achieve its intended purpose. More specifically, a therapeutically-effective amount means an amount of a compound or composition effective to prevent, stabilize, alleviate or ameliorate symptoms of disease, worsening of the disease, or prolong the survival of the subject being treated. Determination of a therapeutically-effective amount is well within the capability of those skilled in the art, especially in light of the detailed disclosure provided herein.

Doses and Combinations

The exact formulation, route of administration and dosage for the pharmaceutical compositions of the present invention can be chosen by the individual physician in view of the patient's condition. (See e.g., Fingl et al. 1975, in "*The Pharmacological Basis of Therapeutics*", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds and insulin mentioned in the present disclosure, human dosages for treatment of at least some condition have been established. Established human dosages of naltrexone include 50, 100, and 150 mg per day. Established human dosages of bupropion include 300, 400, and 450 mg per day. Thus, in most instances, the present invention will use those same dosages, or dosages that are between about 0.1% and 500%, about 1% and about 500%, about 10% and about 500%, about 25% and about 500%, about 50% and about 500%, about 100% and about 500%, about 250% and about 500%, about 0.1% and about 250%, about 1% and about 250%, about 10% and about 250%, about 25% and about 250%, about 50% and about 250%, about 100% and about 250%, about 0.1% and about 100%, about 1% and about 100%, about 10% and about 100%, about 25% and about 100%, about 50% and about 100%, about 0.1% and about 50%, about 1% and about 50%, about 10% and about 50%, about 25% and about 50%, about 0.1% and about 25%, about 1% and about 25%, about 10% and about 25%, about 0.1% and about 10%, about 1% about and 10%, or about 0.1% and 1% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals. For the doses of insulin, a lower amount can be required as a unit dose, in some embodiments, due to the effect of the other compounds. However, this lower dose can readily be determined by using the teachings and methods disclosed herein and the knowledge of one of skill in the art.

As will be appreciated by one of skill in the art, the amount of the various compounds (e.g., opioid antagonist, psychotherapeutic, and/or anticonvulsant) and insulin can vary depending upon the particular situation. The exact doses or amounts can be determined by one of skill in the art in light of the present disclosure.

The amount of insulin administered with or in each composition can vary, depending upon the particular circumstances in which it is to be used. In some embodiments, only a fraction of a unit (e.g., 0.1-0.2, 0.2-0.3, 0.3-0.4, 0.4-0.5, 0.5-0.6, 0.6-0.7, 0.7-0.8, 0.9-0.99 U) to one or two units of insulin is included. Such levels of insulin can be useful for basal insulin treatment. The amount of additional compounds (e.g., anticonvulsant or psychotherapeutic) can be adjusted accordingly. In other embodiments, the amount of insulin is higher, for example, 2-5, 5-10, 10-15, or 15-20 U. Of course, the amount of insulin to add can depend upon the activity of the subject, the size and sex of the subject, as well as the amount of time that the insulin is supposed to alter a patient's blood sugar. Additionally, as the above compounds increase a subject's insulin sensitivity, the amount of the above compounds can also lower the amount of insulin to add. For example, 99-90, 90-80, 80-70, 70-60, 60-50, 50-40, 40-30, 30-20, 20-10, 10-1% of the above amounts of insulin can be used depending upon the amount of the above compounds used.

Although the exact dosage of the compounds (e.g., opioid antagonist, psychotherapeutic, and/or anticonvulsant) will be determined on a drug-by-drug basis, in most cases, some generalizations regarding the dosage can be made. The daily dosage regimen for an adult human patient may be, for example, an oral dose of between 0.1 mg and 6000 mg of each ingredient, preferably between 1 mg and 5000 mg, e.g. 25 to 5000 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically-acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for a week or more, or for months or years. Particular examples of amounts of the various compounds that can be mixed with insulin are described below.

In some embodiments, the dosage range for lithium carbonate, for an oral dose, will result in blood levels of lithium being between about 0.5 and about 1.5 meq/l. In a preferred embodiment, the lithium carbonate dosage range, for an oral dose, will be about 900 mg/day.

In certain embodiments, the dosage range for valproate, for an oral dose, is in the range of about 250 to about 5000 mg/day. In a preferred embodiment, the valproate dosage range, for an oral dose, will be about 1500 mg/day.

In further embodiments, the dosage range for zonisamide, for an oral dose, is in the range of about 25 to about 600 mg per day. In some embodiments, the dosage is 25 mg per day. In other embodiments, the dosage is 50 mg per day. In yet other embodiments, the dosage is 100 mg per day.

In further embodiments, the dosage range for mitrazepine, for an oral dose, is in the range of about 5 to about 500 mg per day. In some embodiments, the dosage is 8 mg per day. In other embodiments, the dosage is 16 mg per day. In yet other embodiments, the dosage is 32 mg per day. In some embodiments, the dosage is 15 mg per day. In other embodiments, the dosage is 30 mg per day. In yet other embodiments, the dosage is 45 mg per day.

In other embodiments, the dosage range for venlafaxinor venlafaxin XR, for an oral dose, is in the range of about 20 mg to about 600 mg per day. In some embodiments, the dosage is 25 mg per day. In other embodiments, the dosage is 37.5 mg per day. In yet other embodiments, the dosage is 50 mg per day. In some embodiments, the dosage is 75 mg per day. In other embodiments, the dosage is 100 mg per day. In yet other embodiments, the dosage is 150 mg per day.

As noted above, any of the above compounds can further be mixed with insulin in either a method or composition.

Dosage amount and interval may be adjusted individually to provide plasma levels of the compound(s) and/or insulin which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen that maintains plasma levels above the MEC for 10-90% of the time, preferably between 30-90% and most preferably between 50-90%. The relevant time period need not be the whole and can be, for example, during feeding, or during sleep.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The composition or compounds may, if desired, be presented in a pack or dispenser device which may contain one or more unit dosage forms containing the active ingredient(s). The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. In some embodiments, the above pack or kit above comprises the compounds (e.g., opioid antagonist, psychotherapeutic, and/or anticonvulsant) as well as insulin. The kit can also contain a means for administering the insulin, such as a needle and syringe for subcutaneous injection.

It will be understood by those of skill in the art that numerous and various modifications can be made without departing from the spirit of the present invention. Therefore, it should be clearly understood that the forms of the present invention are illustrative only and are not intended to limit the scope of the present invention. Additionally, the various sections of the above text are for ease of use only and are not meant to exclude relevant sections from one part from another part.

All documents and other information sources cited above are hereby incorporated in their entirety by reference, as are Gadde et al, *Obesity Res.* 9:544-551 (2001) and Gadde et al, *JAMA* 289:1820-1825 (2003).

As will be appreciated by one of skill in the art, any of the above methods or compositions that include insulin can be modified so that they do not include insulin. Likewise, any of the above methods or compositions that do not include insulin can be modified so that they include insulin if they do not already explicitly include insulin. For example, while a pharmaceutical composition comprising insulin and an α-MSH activity enhancer or psychotherapeutic can be administered to a patient as a method for inhibiting a blood-glucose condition, a patient can get the benefit from simply the administration of the α-MSH activity enhancer, and thus the insulin need not be added as part of the method itself. Methods of administering the BGM compositions to a subject as described herein may comprise obtaining a measurement of the subject's blood glucose level. Such measurements may be made by the subject or by another person, such as by a medical professional, using methods known to those skilled in the art. In an embodiment, a method of administering the BGM compositions to a subject as described herein further comprises adjusting a dosage of the composition after obtaining the measurement of the subject's blood glucose level. In an embodiment, a method of administering the BGM compositions to a subject as described herein further comprises providing dietary instructions to the subject.

An embodiment provides a package comprising a BGM composition as described herein, along with instructions advising the reader to monitor the blood glucose level of the intended recipient of the BGM composition.

Some Embodiments of the Invention

Some of the embodiments of the present invention are as follows:

In a first embodiment, the invention relates to a composition for the inhibition a blood-glucose condition comprising a psychotherapeutic agent, an anticonvulsant, or both the psychotherapeutic agent and the anticonvulsant, and insulin.

In the second embodiment, the invention relates to a composition of the first embodiment, wherein said psychotherapeutic agent is selected from the group consisting of bupropion, lithium carbonate, lithium citrate, valproate, olanzapine, mixtures thereof, and pharmaceutically acceptable salts or prodrugs thereof.

In the third embodiment, the invention relates to a composition of the first embodiment wherein said anticonvulsant is selected from the group consisting of topiramate and zonisamide, and pharmaceutically-acceptable salts or prodrugs thereof, and combinations thereof.

In the fourth embodiment, the invention relates to a composition of the first embodiment, wherein said anticonvulsant is zonisamide.

In the fifth embodiment, the invention relates to a composition of the fourth embodiment, wherein said psychotherapeutic agent is lithium carbonate or lithium citrate.

In the sixth embodiment, the invention relates to a composition of the fourth embodiment, wherein said psychotherapeutic agent is valproate.

In the seventh embodiment, the invention relates to a composition of the first embodiment, wherein said psychotherapeutic agent is a salt of lithium and said anticonvulsant is zonisamide.

In the eighth embodiment, the invention relates to a composition of the first embodiment, wherein said psychotherapeutic agent is valproic acid, or a pharmaceutically-acceptable salt, ester, amide, or prodrug thereof, and said anticonvulsant is zonisamide.

In the ninth embodiment, the invention relates to a composition of the first embodiment, wherein said psychotherapeutic agent is mirtazapine and said anticonvulsant is zonisamide.

In the tenth embodiment, the invention relates to a composition of the first embodiment, wherein said psychotherapeutic agent is bupropion and said anticonvulsant is zonisamide.

In the eleventh embodiment, the invention relates to a composition of the first embodiment, wherein said psychotherapeutic agent is setiptiline and said anticonvulsant is zonisamide.

In the twelfth embodiment, the invention relates to a composition of the first embodiment, wherein said psychotherapeutic agent is bupropion and said anticonvulsant is topiramate.

In the thirteenth embodiment, the invention relates to a composition of the first embodiment, wherein said psychotherapeutic agent is a combination of bupropion and mirtazapine and said anticonvulsant is zonisamide.

In the fourteenth embodiment, the invention relates to a composition of the first embodiment, wherein said psychotherapeutic agent is a combination of bupropion and setiptiline and said anticonvulsant is zonisamide.

In the fifteenth embodiment, the invention relates to a method of inhibiting a blood-glucose condition comprising identifying a subject in need thereof, administering to the subject a psychotherapeutic agent, an anticonvulsant, or both to the subject.

In the sixteenth embodiment, the invention relates to a method of the fifteenth embodiment, wherein the psychotherapeutic agent is selected from the group consisting of lithium carbonate, lithium citrate, and valproate, and pharmaceutically-acceptable salts, esters, amides, or prodrugs thereof, and said anticonvulsant is zonisamide.

In the seventeenth embodiment, the invention relates to a method of the fifteenth embodiment, wherein the psychotherapeutic agent is selected from the group consisting of mirtazapine, and setiptiline, and pharmaceutically-acceptable salts, esters, amides, or prodrugs thereof, and said anticonvulsant is zonisamide.

In the eighteenth embodiment, the invention relates to a method of the fifteenth embodiment, further comprising administering insulin, wherein the insulin is administered at approximately the same time as the psychotherapeutic agent, the anticonvulsant, or both is administered to the individual.

In the nineteenth embodiment, the invention relates to a method of the fifteenth embodiment, further comprising administering insulin, wherein said insulin is administered after the psychotherapeutic agent, the anticonvulsant, or both is administered to the subject.

In the twentieth embodiment, the invention relates to a method of the fifteenth embodiment, further comprising administering insulin to the subject, wherein the insulin is administered before the psychotherapeutic agent, the anticonvulsant, or both is administered to the subject.

In the twenty first embodiment, the invention relates to a method of inhibiting loss of insulin sensitivity, said method comprising identifying a subject in need of a inhibition in the loss of insulin sensitivity and administering a compound selected from the group consisting of a psychotherapeutic agent, an anticonvulsant, an opioid receptor antagonist or some combination thereof.

In the twenty second embodiment, the invention relates to a pharmaceutical composition for the inhibition of a blood-glucose condition comprising a psychotherapeutic agent, an opioid antagonist, or both the psychotherapeutic agent and the opioid antagonist and insulin.

In the twenty third embodiment, the invention relates to a composition of the twenty second embodiment, wherein the opioid antagonist comprises naltrexone.

In the twenty fourth embodiment, the invention relates to a composition comprising any of the above compositions, wherein the amount of the compound(s) is no more than about an effective amount for increasing insulin sensitivity.

In the twenty fifth embodiment, the invention relates to a composition comprising a psychotherapeutic agent, an anticonvulsant, or some combination thereof, wherein said psychotherapeutic agent and said anticonvulsant are present in at least an effective amount.

In the twenty sixth embodiment, the invention relates to the method of the twenty first embodiment, wherein the psychotherapeutic agent is bupropion and the opioid receptor antagonist is naltrexone.

In the twenty seventh embodiment, the invention relates to the method of the twenty first embodiment, wherein the psychotherapeutic agent is fluoxetine and the opioid receptor antagonist is naltrexone.

In the twenty eighth embodiment, the invention relates to a composition for the inhibition of a blood-glucose condition comprising an anticonvulsant and an opioid receptor antagonist.

In the twenty ninth embodiment, the invention relates to a composition for the inhibition of a blood-glucose condition comprising a psychotherapeutic agent and an opioid receptor antagonist.

In the thirtieth embodiment, the invention relates to the twenty ninth embodiment in which the psychotherapeutic agent is bupropion and the opioid receptor antagonist is naltrexone.

In the thirty first embodiment, the invention relates to the twenty ninth embodiment in which the psychotherapeutic agent is fluoxetine and the opioid receptor antagonist is naltrexone.

In the thirty second embodiment, the invention relates to a composition for inhibition of a blood-glucose condition, wherein said composition comprises a psychotherapeutic agent and an anticonvulsant.

In the thirty third embodiment, the invention relates to the composition of the thirty second embodiment, in which the psychotherapeutic agent is olanzapine and the anticonvulsant is zonisamide.

In the thirty fourth embodiment, the invention relates to a method of inhibition of a blood-glucose condition, comprising identifying a subject in need thereof, and administering both a psychotherapeutic agent and an anticonvulsant to the subject.

In the thirty fifth embodiment, the invention relates to the method of the thirty fourth embodiment in which the psychotherapeutic agent is olanzapine and the anticonvulsant is zonisamide.

In the thirty sixth embodiment, the invention relates to a composition for reversing insulin resistance caused by administration of a psychotherapeutic agent or an anticonvulsant, wherein said composition comprises a psychotherapeutic agent and an anticonvulsant.

In the thirty seventh embodiment, the invention relates to the composition of the thirty sixth embodiment, in which the psychotherapeutic agent is olanzapine and the anticonvulsant is zonisamide.

In the thirty eighth embodiment, the invention relates to a method of reversing a blood-glucose condition caused by administration of a psychotherapeutic agent or an anticonvulsant, comprising identifying a subject in need thereof, and administering a psychotherapeutic agent and an anticonvulsant to the subject.

In the thirty ninth embodiment, the invention relates to the method of the thirty eighth embodiment, in which the psychotherapeutic agent is olanzapine and the anticonvulsant is zonisamide.

EXAMPLES

The examples below are non-limiting and are merely representative of various aspects of the invention.

Example 1

Use of Zonisamide

Individuals taking insulin are identified. Each individual is instructed to take one 25 mg tablet of zonisamide on a daily basis, in addition to the insulin therapy.

The individuals are monitored for a period of months. It is recommended that the dosage be adjusted so that each individual remains sensitive to their dose of insulin and to maintain a healthy blood sugar level; thus the insulin levels may have to be decreased.

The dosage of zonisamide can be from about 25 mg to about 800 mg per day, generally given once per day or divided (e.g., equally) into multiple doses. Preferably, the dose is from about 100 mg to about 600 mg per day, more preferably, the dose is from about 200 mg to about 400 mg per day. However, it may be necessary to use dosages outside these ranges. Zonisamide tablets are usually made and marketed in 25 mg, 50 mg, and 100 mg doses. Individual tablets, or combination of tablets can be used to achieve the desired dosing. The insulin is administered subcutaneously in amounts varying from 1-10 units.

Example 2

Use of Topiramate

Individuals taking insulin are identified. Each individual is instructed to take one 25 mg tablet of topiramate on a daily basis, in addition to the insulin therapy.

The individuals are monitored for a period of months. It is recommended that the dosage be adjusted so that each remains sensitive to their current dosing scheme of insulin.

The dosage of topiramate can be from about 25 mg to about 1600 mg, preferably from about 50 mg to about 600 mg, more preferably from about 100 mg to about 400 mg. However, it may be necessary to use dosages outside these ranges.

Alternatively, upon the administration of the topiramate, the dosing scheme of the individual's insulin is reduced by 10%. As this reduction in insulin, in combination with topiramate, will not adversely impact the individual, lower doses of insulin will be effective for maintaining the individual's desired blood sugar levels and the risk that the individual will develop insulin resistance is reduced.

Example 3

Combination of Zonisamide and Mitrazepine

Individuals taking insulin are identified. Each individual's dosing scheme for insulin is noted as well as the resulting blood sugar of the individual from the particular doses of insulin.

Each individual is instructed to take one tablet of zonisamide on a daily basis, in addition to one tablet of mitrazepine on a daily basis, and the individual's dosing scheme for insulin is reduced gradually over time. Initially, the drugs are administered as follows: 8 mg mitrazepine and 64 mg zonisamide; or 16 mg mitrazepine and 128 mg zonisamide; or 32 mg mitrazepine and 252 mg zonisamide; generally with an mitrazepine/zonisamide ratio of 1:8. Over a period of weeks, the individual's dosing scheme of insulin is reduced by 5%, then 10, 20, 30, 40, 50% and so on. During this reduction in administered insulin levels, the individual's blood sugar levels are monitored. The reduction in insulin level is continued until the individual's blood sugar level is no longer safe. Thus, the ability of these compounds to sensitize an individual to insulin, allowing the individual to take less insulin, can be determined.

If the initial dosages are not effective, they can be increased.

Example 4

Combination of Zonisamide and Paroxetine

Individuals suffering from insulin resistance are identified. The amount of insulin administered to the individual (initial level of insulin) and the resulting impact of that insulin on the individual's blood sugar is determined.

Each individual is instructed to take one tablet of zonisamide on a daily basis, in addition to one tablet of paroxetine on a daily basis, in addition to their normal dose of insulin. Initially, the drugs are administered as follows: 10 mg paroxetine and 60 mg zonisamide; or 20 mg paroxetine and 120 mg zonisamide; or 30 mg paroxetine and 180 mg zonisamide; or 40 mg paroxetine and 240 mg zonisamide; generally with a paroxetine/zonisamide ratio of 1:6. The amount of insulin can vary, and is generally between about 1 unit and 10 units.

The individuals are monitored for a period of months. Following this, the amount of insulin administered is lowered to a point beneath the initial level of insulin, and closer to the amount of insulin that was administered to the individual before the individual suffered from insulin resistance (pre-insulin resistance level of insulin). The blood sugar levels of the individual are then examined to determine if the lower level of insulin is still effective in maintaining the individual's blood sugar levels at the desired levels. The above compounds will be effective in reversing insulin resistance.

If the initial dosages are not effective, they can be increased.

Example 5

Combination of Zonisamide and Bupropion

Individuals at risk of developing insulin resistance are identified. Each individual is instructed to take one 50 mg tablet of zonisamide on a daily basis. In addition, each individual is instructed to take one 250 mg tablet of bupropion on a daily basis.

The individuals are monitored for a period of months. It is recommended that the dosage be adjusted so that each individual maintains or reduces their daily intake of insulin to obtain their desired blood sugar levels.

If the initial dosage is not effective, then the bupropion dosage can be increased by 20 mg intervals up to 3000 mg per day. If the initial dosage results in a more rapid increase in insulin sensitivity than the above rate, the dosage of each of zonisamide or bupropion can be reduced.

Example 6

Treatment of Type 2 Diabetes

An individual with Type 2 diabetes is identified. The individual's blood sugar is monitored as well as the daily dose of insulin. The individual is administered 50 mg of zonisamide and 250 mg of bupropion per day. The individual's blood sugar is again measured. The amount of insulin administered to the individual will be decreased accordingly to maintain the desired blood sugar levels. If there is no need for a decrease in the amount of insulin (e.g, the individual's previous dose of insulin is not too much), then the amount of zonisamide and bupropion can be increased until the amount of insulin administered can be decreased. Supplemental amounts of insulin can still be administered to the individual, if required. Thus, one can treat Type 2 diabetes.

This example can be used for any of the above compounds and combinations thereof to determine the amount and frequency of each of the compounds to be administered. This can also be used for treating and/or inhibiting insulin resistance and Type 2 diabetes.

Example 7

Combination of Naltrexone and Fluoxetine (Insulin Tolerance Test)

Mice (n=3) were fed overnight then given an intraperitoneal (I.P.) injection of one of the following: vehicle, fluoxetine (8.5 mg/kg), naltrexone (2.5 mg/kg) or fluoxetine+naltrexone (8.5 mg/kg fluoxetine, 2.5 mg/kg naltrexone). A baseline blood glucose determination was made two hours post-injection. Mice were then given a standard I.P. injection of insulin. Blood glucose levels were then followed for two hours (at 15 min, 30 min, 1 h and 2 h). The results are summarized in Tables 1-4 for vehicle, fluoxetine, naltrexone and naltrexone+bupropion, respectively. Glucose levels are in mg/dl.

TABLE 1

| vehicle | | | | |
|---|---|---|---|---|
| Baseline | 15 min | 30 min | 1 h | 2 h |
| 126 | 76 | 85 | 89 | 187 |
| 123 | 79 | 96 | 112 | 137 |
| 139 | 78 | 72 | 96 | 143 |

TABLE 2

| fluoxetine | | | | |
|---|---|---|---|---|
| Baseline | 15 min | 30 min | 1 h | 2 h |
| 135 | 63 | 93 | 118 | 228 |
| 161 | 82 | 90 | 138 | 169 |
| 145 | 84 | 80 | 89 | 189 |

TABLE 3

| naltrexone | | | | |
|---|---|---|---|---|
| Baseline | 15 min | 30 min | 1 h | 2 h |
| 137 | 68 | 84 | 106 | 181 |
| 111 | 62 | 82 | 80 | 175 |
| 134 | 65 | 81 | 127 | 186 |

TABLE 4

| naltrexone + fluoxetine | | | | |
|---|---|---|---|---|
| Baseline | 15 min | 30 min | 1 h | 2 h |
| 148 | 34 | 56 | 71 | not determined |
| 102 | 33 | 97 | 91 | 95 |
| 120 | 34 | 57 | 81 | 78 |

The data show that, at these dosages, neither fluoxetine nor naltrexone alone had an effect on insulin tolerance beginning 2 hours post-injection since glucose levels in mice injected with either of these compounds do not differ from mice injected with vehicle at each time point tested. However, the combination of fluoxetine and naltrexone had a significant effect on insulin resistance since glucose levels were significantly lower after two hours compared to mice which were administered either compound alone. Thus, this combination was effective in inhibiting insulin resistance.

Example 8

Combination of Naltrexone and Bupropion (Insulin Tolerance Test)

The same study described in Example 7 was performed, except that mice (n=12) were treated with vehicle, naltrexone (3 mg/kg), bupropion (50 mg/kg) or naltrexone (3 mg/kg)+ bupropion (50 mg/kg). Total areas under the curve (AUC) were calculated based on glucose levels at each time point for each mouse. AUC is a summation of glucose levels observed at each time point. AUC values for the mice were (ND=not determined):

Vehicle: 13575, 10485, ND, 12038, 9353, 9990, 8160, ND, 14258, 10883, 12555 and 10065 (mean=11136.2)

Bupropion: 13613, 9083, 11438, ND, 14003, 9668, 8003, 10725, 8715, 8715, 12038, 11280 (mean=10661.91, which is 95.7% of vehicle AUC, representing a 4.3% decrease in AUC).

Naltrexone: 11445, ND, 7208, 14783, 7215, 13058, 10493, 9045, 8003, 10193, 10763, 15990 (mean=10745.09, which is 96.5% of vehicle AUC, representing a 3.5% decrease in AUC).

Naltrexone+Bupropion: 7740, 7680, 12300, 8685, ND, 8775, ND, 8550, 12300, 8625, ND, ND (mean=9331.875, which is 83.8% of vehicle AUC, representing a 16.2% decrease in AUC).

Thus, the administration of bupropion and naltrexone exhibited a synergistic effect in inhibiting insulin resistance compared to either compound administered alone. Since naltrexone resulted in a 3.5% decrease and bupropion resulted in a 4.3% decrease, the co-administration would have been expected to reduce the AUC by 7.8%. In fact, the observed effect was twice the expected effect.

Example 9

Combination of Olanzapine and Zonisamide (Insulin Tolerance Test)

Female Sprague-Dawley rats, weighing about 235 grams at the start of the experiment were used. They were trained to sham injections, using the zonisamide vehicle for 2 weeks before the study commenced. Under isoflurane anesthesia, Alzet osmotic minipumps (2 ml2) were implanted subcutaneously, between the shoulder blades. The rats were subsequently returned to their home cages after recovery. The minipumps delivered 5 μL per hour for 14 days. Olanzapine was dissolved in 1.5% lactic acid in $dH_2O$. Zonisamide was dissolved in 10% DMSO, 13.4% EtOH, 20.1% PPG, and 66.5% saline. Olanzapine dose was 1.75 mg/day. The animals were housed individually and supplied with standard laboratory chow. Food consumed and animal weights were recorded every days. There were 5 animals in the control (vehicle) group, 5 animals in the zonisamide only group, 5 animals in the olanzapine only group, and 6 animals in the olanzapine+zonisamide group.

Rats were allowed to recover after pump implantation, and then received twice daily injections of zonisamide 26 mg/kg. Blood was drawn by saphenous venepuncture 13 days after olanzapine implant, 6 days after twice daily zonisamide injections began and blood glucose levels were measured by hand-held glucometer (Roche Accucheck, Advantage) with glucose strips. The results are shown below (Table 5).

TABLE 5

| olanzapine + zonisamide | |
|---|---|
| | Average |
| Vehicle | |
| Blood Glucose mg/dl | 92.2 |
| Olanzapine 1.75 mg/day | |
| Blood Glucose mg/dl | 120.4 |
| Zonisamide 26 mg/kg | |
| Blood Glucose mg/dl | 117.6 |
| Olanzapine + Zonisamide | |
| Blood Glucose mg/dl | 97.66667 |

Thus, while either compound administered alone resulted in increased insulin resistance (elevated glucose levels), the co-administration of olanzapine and zonisamide inhibited insulin resistance and resulted in blood glucose levels similar to vehicle-treated animals.

What is claimed is:

1. A method of treating insulin resistance, comprising:
identifying a subject having a blood-glucose condition characterized by insulin resistance in need of treatment; and
administering to the subject an amount of a composition that is effective to treat the insulin resistance, wherein the composition comprises naltrexone or a pharmaceutically acceptable salt thereof and bupropion or a pharmaceutically acceptable salt thereof, wherein the amount of the naltrexone or pharmaceutically acceptable salt thereof is about 25 mg per day to about 50 mg per day, and wherein the amount of the bupropion or pharmaceutically acceptable salt thereof is about 200 mg per day to about 400 mg per day.

2. The method of claim 1, wherein the condition is Type 2 diabetes.

3. The method of claim 1, wherein the naltrexone or pharmaceutically acceptable salt thereof is administered to the subject separately from the bupropion or pharmaceutically acceptable salt thereof.

4. The method of claim 1, wherein the composition further comprises insulin.

5. The method of claim 1, further comprising obtaining a measurement of the subject's blood glucose level.

6. The method of claim 5, further comprising adjusting a dosage of the composition after obtaining the measurement of the subject's blood glucose level.

7. The method of claim 1, further comprising providing dietary instructions to the subject.

8. The method of claim 1, wherein at least one of the naltrexone or pharmaceutically acceptable salt thereof and the bupropion or pharmaceutically acceptable salt thereof is in a sustained release formulation.

9. The method of claim 1, wherein each of the naltrexone or pharmaceutically acceptable salt thereof and the bupropion or pharmaceutically acceptable salt thereof is in a sustained release formulation.

10. The method of claim 1, wherein the naltrexone or pharmaceutically acceptable salt thereof and the bupropion or pharmaceutically acceptable salt thereof are in a single oral dosage form.

11. The method of claim 10, wherein the single oral dosage form is in the form of a tablet, pill, or capsule.

12. A method of treating insulin resistance, comprising:
identifying a subject having a blood-glucose condition characterized by insulin resistance in need of treatment; and
administering to the subject an amount of a composition that is effective to treat the insulin resistance, wherein the composition comprises a sustained-release naltrexone formulation and a sustained-release bupropion formulation or pharmaceutically acceptable salts thereof, wherein the amount of the naltrexone or pharmaceutically acceptable salt thereof is about 25 mg per day to about 50 mg per day, and wherein the amount of the bupropion or pharmaceutically acceptable salt thereof is about 200 mg per day to about 400 mg per day, and wherein the composition is in a single oral dosage form.

13. The method of claim 12, wherein the condition is Type 2 diabetes.

14. The method of claim 12, wherein the composition further comprises insulin.

15. The method of claim 12, wherein the single oral dosage form is in the form of a tablet, pill, or capsule.

16. The method of claim 1, wherein the amount of the naltrexone or pharmaceutically acceptable salt thereof is about 25 mg per day to about 38 mg per day, and wherein the amount of the bupropion or pharmaceutically acceptable salt thereof is about 300 mg per day to about 400 mg per day.

17. The method of claim 16, wherein the subject is obese.

18. The method of claim 1, wherein the subject is obese.

19. The method of claim 12, wherein the amount of the naltrexone or pharmaceutically acceptable salt thereof is about 25 mg per day to about 38 mg per day, and wherein the amount of the bupropion or pharmaceutically acceptable salt thereof is about 300 mg per day to about 400 mg per day.

20. The method of claim 19, wherein the subject is obese.

21. The method of claim 12, wherein the subject is obese.

22. The method of claim 1, wherein the condition is pre-diabetes.

23. The method of claim 22, wherein the subject is obese.

24. The method of claim 12, wherein the condition is pre-diabetes.

25. The method of claim 24, wherein the subject is obese.

26. The method of claim 16, wherein the condition is pre-diabetes.

27. The method of claim 26, wherein the subject is obese.

28. The method of claim 19, wherein the condition is pre-diabetes.

29. The method of claim 28, wherein the subject is obese.

30. The method of claim 2, wherein the subject is obese.

31. The method of claim 13, wherein the subject is obese.

* * * * *